(12) United States Patent
Van Gogh

(10) Patent No.: US 8,192,506 B2
(45) Date of Patent: Jun. 5, 2012

(54) COMPOSITIONS FOR DYEING KERATIN-CONTAINING FIBERS

(75) Inventor: Kelly Van Gogh, New York, NY (US)

(73) Assignee: Kelly Van Gogh, Inc., New York, NY (US)

( * ) Notice: Subject to any disclaimer, the term of this patent is extended or adjusted under 35 U.S.C. 154(b) by 0 days.

(21) Appl. No.: 13/242,114

(22) Filed: Sep. 23, 2011

(65) Prior Publication Data

US 2012/0055840 A1  Mar. 8, 2012

Related U.S. Application Data

(63) Continuation-in-part of application No. 12/875,058, filed on Sep. 2, 2010, now Pat. No. 8,052,762.

(51) Int. Cl.
*A61Q 5/10* (2006.01)

(52) U.S. Cl. ............. 8/405; 8/406; 8/408; 8/412; 8/421; 8/423; 8/435

(58) Field of Classification Search ............... 8/405, 406, 8/408, 410, 412, 421, 423, 435
See application file for complete search history.

(56) References Cited

U.S. PATENT DOCUMENTS

| | | | |
|---|---|---|---|
| 4,776,856 | A | 10/1988 | Tennigkeit et al. |
| 4,808,190 | A | 2/1989 | Grollier et al. |
| 5,529,583 | A | 6/1996 | Lim et al. |
| 5,618,523 | A | 4/1997 | Zysman et al. |
| 5,672,180 | A | 9/1997 | Lim et al. |
| 6,045,590 | A | 4/2000 | Lim et al. |
| 6,251,378 | B1 | 6/2001 | Laurent et al. |
| 6,312,677 | B1 | 11/2001 | Millequant et al. |
| 6,537,328 | B1 | 3/2003 | Lang et al. |
| 6,554,871 | B2 * | 4/2003 | Braun ............................. 8/409 |
| 7,060,108 | B2 | 6/2006 | Morita et al. |
| 7,179,302 | B2 | 2/2007 | Boswell et al. |
| 7,186,275 | B2 | 3/2007 | Boswell et al. |
| 7,429,276 | B2 | 9/2008 | Wood et al. |
| 8,052,762 | B1 | 11/2011 | Van Gogh et al. |
| 2007/0020208 | A1 | 1/2007 | Gutkowski et al. |
| 2008/0034510 | A1 | 2/2008 | Speckbacher et al. |
| 2008/0194708 | A1 | 8/2008 | Hossel et al. |
| 2009/0068136 | A1 | 3/2009 | Beumer et al. |
| 2010/0040573 | A1 | 2/2010 | Castro et al. |

\* cited by examiner

*Primary Examiner* — Eisa Elhilo
(74) *Attorney, Agent, or Firm* — Richard S. Echler

(57) ABSTRACT

Disclosed herein are compositions suitable for use in dyeing keratin-containing fibers. Further disclosed herein are colorant systems and compositions comprising the colorant systems. Also disclosed are kits comprising one or more colorant systems and an activator composition.

20 Claims, No Drawings

COMPOSITIONS FOR DYEING KERATIN-CONTAINING FIBERS

PRIORITY

This application is a Continuation-In-Part of U.S. application Ser. No. 12/875,058, filed Sep. 2, 2010 now U.S. Pat. No. 8,052,762, which is incorporated herein by reference in its entirety.

FIELD

Disclosed herein are compositions suitable for use in dyeing keratin-containing fibers. Further disclosed herein are colorant systems and compositions comprising the colorant systems. Also disclosed are kits comprising one or more colorant systems and an activator composition.

BACKGROUND

Dyeing of keratin-containing fibers, especially human hair is a marriage between art and science. It is a clear example of tuning an aesthetically desired result with the ability to deliver that result by way of a chemical reaction that takes place at the time of use; there is no going back to the laboratory and trying again if the outcome is not what the user desires. As such, the formulation of a keratin-containing fiber coloring composition must not be susceptible to the slight to moderate variations in product use instructions that may occur during application.

In addition, hair coloring is not done in a void; the compositions are applied to keratin-containing fibers that vary greatly from subject to subject due to an array of variables, inter alia, condition of the hair and scalp, previously applied treatments, and the morphology of the fibers themselves. Hair can be fine, thick, dense, or sparse. Therefore, any composition for use in dyeing human hair must be able to evenly coat the fibers, as well as to permeate the surface of the fibers themselves regardless of the condition of the fiber itself.

DETAILED DESCRIPTION

The materials, compounds, compositions, articles, kits and methods described herein may be understood more readily by reference to the following detailed description of specific aspects of the disclosed subject matter and the Examples included therein. Before the present materials, compounds, compositions, articles, devices, kits and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

All percentages, ratios and proportions herein are by weight, unless otherwise specified. All temperatures are in degrees Celsius (° C.) unless otherwise specified. All values in the disclosed TABLES are in weight/weight percentage, i.e., "a composition comprising 15% by weight" is understood to comprise 0.15 of its mass the disclosed ingredient. As such, a weight percent of a component, unless specifically stated to the contrary, is based on the total weight of the formulation or composition in which the component is included.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

"Admixture" or "blend" is generally used herein means a physical combination of two or more different components.

As used herein, by a "subject" is meant an individual, i.e., a human or animal having keratin-containing fiber (in general, hair) onto which subject's fibers is being applied one or more of the disclosed compositions.

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "a phenylsulfamic acid" includes mixtures of two or more such phenylsulfamic acids, reference to "the compound" includes mixtures of two or more such compounds, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

The term "keratinous tissue," as used herein, refers to keratin-containing layers disposed as the outermost protective covering of mammals which includes, but is not limited to, skin, hair, toenails, fingernails, cuticles, hooves, etc.

The term "colorant precursor," as used herein, means compounds that can function as oxidative dye precursors, coupling agents, or in some instances the compounds can function as both oxidative dye precursors and coupling agents. The disclosed colorant precursors react with one another in a manner understood by the formulator when acted upon by a catalyst to form compound admixtures that provide a dye, hue, tint, color, and the like to keratin-containing fibers.

The term "topical application," as used herein, means to apply or spread the compositions of the present invention onto the surface of the keratinous tissue.

The term "dermatologically acceptable," as used herein, means that the compositions or components thereof so described are suitable for use in contact with human keratinous tissue without undue toxicity, incompatibility, instability, and the like. The term "safe and effective amount" as used herein means an amount of a compound or composition sufficient to significantly induce a positive benefit, preferably a positive keratinous tissue appearance or feel benefit, including independently or in combinations the benefits disclosed herein, but low enough to avoid serious side effects, i.e., to provide a reasonable benefit to risk ratio, within the scope of sound judgment of the skilled artisan.

The term "active ingredient," as used herein, relates to compounds that either alone or together with one or more of the disclosed ingredients is capable of modifying keratin-containing fibers or can modify or improve the application of the composition including stabilizing one or more of the other ingredients, for example, an active ingredient can be a compound that stabilizes the hydrogen peroxide or that maintains a homogeneous composition by eliminating phase separation or undesirable micelle formation. Not included in the definition of "active ingredients" are compounds that are used to dilute or aid in the dissolution of ingredients, for example, water is not an active ingredient.

The term "smoothing" and "softening" as used herein means altering the surface of the keratinous tissue such that its tactile feel is improved.

The term "activator composition," as used herein, means a composition comprising one or more ingredients that when combined with one or more colorant precursors, causes a chemical reaction to occur which affords an admixture of colorants in situ which provide a color to keratin-containing fibers. The artisan will also recognize the terms "developer" and "developer solution" to stand equally well for activator composition.

Dyeing human hair is a skill. It involves proper techniques of application, aesthetic insight, as well as the ability to assess the condition of the hair and adjoining scalp to make critical evaluations and provide not only aesthetic, but hair health counseling to the subject. Moreover, many hair color formulations are formulated so they can be applied by both the consumer and the professional colorist. As such, consistency of delivery while providing options to the user is important to controlled and effective hair coloring products.

What is not applied to hair is a pre-formed dye or color solution. Instead, one or more precursor molecules formulated in precise amounts is applied together with a catalyst that reacts with the various precursor molecules to provide a complex admixture of compounds that when applied to hair result in a desirable color, hue or tint. Human hair, although comprising roughly the same material, inter alia, proteinaceous tissue, varies greatly. Hair can be affected by age, personal habits, occupational factors, race, sex and environment.

Disclosed herein are compositions useful for coloring keratin-containing fibers, especially human hair wherein the compositions provide a more durable color, as well as providing a means for conditioning hair during coloring. In addition, the disclosed compositions allow for greater penetration of the individual hair fiber such that the resulting color, hue or tint is more homogeneous.

The disclosed compositions also allow for the user to adjust the conditions of application to be commensurate with the individual type of hair style or the physical condition of the hair fibers themselves. This increase in control allows the consumer to use the product with more or less frequency and to adapt the amount of resultant color. In addition, the disclosed compositions provide a means for dying hair while conditioning the hair fibers into a more healthy state.

Disclosed are compositions useful for coloring keratin-containing fibers, especially human hair. In use these compositions comprise:
A) a colorant system; and
B) an activator composition.

The disclosed colorant systems comprise:
a) one or more colorant precursors;
b) optionally one or more active ingredients; and
c) optionally one or more diluents or carriers.

The disclosed activator compositions comprise:
a) one or more catalysts;
b) optionally one or more active ingredients; and
c) optionally one or more diluents or carriers.

The disclosed compositions can be formulated such that the colorant system and the activator composition are separately packaged. Alternatively, the disclosed compositions can be formulated such that the colorant system and the activator composition are provided in the same container that has a means for separating the colorant system and activator composition such that the user ruptures or otherwise causes to be admixed the two containers prior to or during usage. The container can have any form compatible with the delivery of the disclosed compositions, i.e., package, bottle, and the like.

The following are non-limiting aspects, embodiments, iterations, and examples of the disclosed coloring compositions. It will become clear to the artisan the full scope of the present disclosure by a reading of the following description and appended claims.

Colorant Systems

The disclosed compositions comprise a colorant system. The colorant systems comprise one or more oxidative dye precursors and one or more coupling agents, both of which are described herein as colorant precursors. One aspect of the disclosed colorant systems relate to compositions comprising:
a) from about 0.5% to about 99.5% by weight of one or more oxidative dye precursors; and
b) from about 0.5% to about 99.5% by weight of one or more coupling agents.

In one embodiment of this aspect, the colorant systems relate to compositions comprising:
a) from about 25% to about 75% by weight of one or more oxidative dye precursors; and
b) from about 25% to about 75% by weight of one or more coupling agents.

In one iteration of this embodiment, the colorant systems relate to compositions comprising:
a) from about 25% to about 75% by weight of one or more oxidative dye precursors;
b) from about 25% to about 75% by weight of one or more coupling agents;
c) one or more carriers or diluents.

Another aspect of the disclosed colorant systems relate to compositions comprising:
a) from about 0.5% to about 49.5% by weight of one or more oxidative dye precursors;
b) from about 0.5% to about 49.5% by weight of one or more coupling agents;
c) from about 50% to about 80% by weight of one or more carriers or diluents.

In a further aspect the disclosed colorant systems relate to compositions comprising:
A) from about 20% to about 50% by weight of an active ingredient composition; and
B) from about 50% to about 80% of one or more carriers.

In one embodiment of this aspect, the disclosed colorant systems relate to compositions comprising:
A) from about 20% to about 50% by weight of an active ingredient composition, comprising:
  i) from about 0.05% to about 5% by weight of a colorant precursor composition;
  ii) from about 0.2% to about 1% by weight of one or more hair detangling agents; and
  iii) the balance active ingredients; and
B) from about 50% to about 80% of one or more carriers.

An iteration of this embodiment relates to a colorant system, comprising:
A) from about 20% to about 50% by weight of an active ingredient composition, comprising:
  i) from about 0.05% to about 5% by weight of a colorant precursor composition;
  ii) from about 0.2% to about 1% by weight of one or more hair detangling agents chosen from $C_{10}$-$C_{22}$ alkyl esters of alkoxylated trimethylolpropane, $C_{10}$-$C_{22}$ alkenyl mono-ene esters of alkoxylated trimethylolpropane, $C_{10}$-$C_{22}$ alkynyl mono-yne esters of alkoxylated trimethylolpropane, and mixtures thereof; and
  iii) optionally the balance adjunct ingredients; and
B) from about 50% to about 80% of one or more carriers.

An example of this iteration relates to a colorant system, comprising:
A) from about 20% to about 50% by weight of an active ingredient composition, comprising:
  i) from about 0.05% to about 5% by weight of a colorant precursor composition;
  ii) from about 0.2% to about 1% by weight of one or more $C_{10}$-$C_{22}$ alkenyl mono-ene esters of alkoxylated trimethylolpropane hair detangling agents chosen from PEG/PPG-120/10 trimethylolpropane trioleate; PEG/PPG-120/10 trimethylolpropane tripalmitate; PEG/PPG-120/10 trimethylolpropane trilinoleate; PEG/PPG-120/10 trimethylolpropane oleate/linoleate/palmitate admixture, and mixtures thereof; and
  iii) the balance adjunct ingredients; and
B) from about 50% to about 80% of one or more carriers.

In another embodiment of this aspect, the disclosed colorant systems relate to compositions comprising:
A) from about 20% to about 50% by weight of an active ingredient composition, comprising:
  i) from about 0.05% to about 5% by weight of a colorant precursor composition;
  ii) from about 0.2% to about 1% by weight of one or more hair detangling agents;
  iii) from about 0.005% to 0.05% by weight of one or more UV absorbers;
  iv) from about 0.1% to about 5% by weight of one or more conditioning agents; and
  v) optionally the balance active ingredients; and
B) from about 50% to about 80% of one or more carriers.

One iteration of this embodiment, the disclosed colorant systems relate to compositions comprising:
A) from about 20% to about 50% by weight of an active ingredient composition, comprising:
  i) from about 0.05% to about 5% by weight of a colorant precursor composition, comprising:
    a) from about 10% to about 90% by weight of the colorant precursor composition, one or more oxidative dye precursors; and
    b) from about 10% to about 90% by weight of the colorant precursor composition, one or more coupling agents;
  ii) from about 0.2% to about 1% by weight of one or more hair detangling agents chosen from $C_{10}$-$C_{22}$ alkyl esters of alkoxylated trimethylolpropane, $C_{10}$-$C_{22}$ alkenyl mono-ene esters of alkoxylated trimethylolpropane, $C_{10}$-$C_{22}$ alkynyl mono-yne esters of alkoxylated trimethylolpropane, and mixtures thereof;
  iii) from about 0.005% to 0.05% by weight of one or more UV absorbers chosen from ethylhexyl methoxycinnamate (octyl methoxycinnamate), methoxydibenzoylmethane, polyoxypropylene, polyoxyethylene ethers of aliphatic alcohols, ethylhexyl salicylate, and polyoxyethylene derivatives of hydroxy fatty acid containing fats and oils, and mixtures thereof;
  iv) from about 0.1% to about 1.5% by weight of one or more conditioning agents chosen from polyalkylene glycols, polypropylene glycols, polyalkylene glycol/polypropylene glycol copolymers; and
  v) the balance one or more adjunct ingredients chosen from moisturizers, chelating agents, anti-oxidation agents, pH adjusters, emulsifiers, shine agents, solubilizers, fragrances, pearlizers, and mixtures thereof; and
B) from about 50% to about 80% of one or more carriers.

Oxidative Dye Precursors

In one aspect the disclosed keratin-comprising fiber dyeing compositions comprise one or more oxidative dye precursors. One category of oxidative dye precursors that can be used in the disclosed colorant systems includes 1,4-phenylenediamine and derivatives thereof. Non-limiting examples include 1,4-phenylenediamine, 2-methylbenzene-1,4-diamine, 2-chloro-benzene-1,4-diamine, N-phenylbenzene-1,4-diamine, N-(2-ethoxyethyl)benzene-1,4-diamine, 2-[(4-amino-phenyl)-(2-hydroxyethyl)-amino]-ethanol, (commonly known as N,N-bis(2-hydroxyethyl)-1,4-phenylenediamine) (2,5-diaminophenyl)methanol, 1-(2'-hydroxyethyl)-2,5-diaminobenzene, 2-(2,5-diaminophenyl)-ethanol, N-(4-aminophenyl)benzene-1,4-diamine, 2,6-dimethylbenzene-1,4-diamine, 2-isopropyl-benzene-1,4-diamine, 1-[(4-aminophenyl)amino]-propan-2-ol, 2-propylbenzene-1,4-diamine, 1,3-bis[(4-aminophenyl)(2-hydroxyethyl)amino]propan-2-ol, $N^4,N^4$,2-trimethylbenzene-1,4-diamine, 2-methoxy-benzene-1,4-diamine, 1-(2,5-diaminophenyl)ethane-1,2-diol, 2,3-dimethyl-benzene-1,4-diamine, N-(4-amino-3-hydroxyphenyl)acetamide, 2,6-diethylbenzene-1,4-diamine, 2,5-dimethylbenzene-1,4-diamine, 2-thien-2-ylbenzene-1,4-diamine, 2-thien-3-ylbenzene-1,4-diamine, 2-pyridin-3-yl-benzene-1,4-diamine, 1,1'-biphenyl-2,5-diamine, 2-(methoxymethyl)benzene-1,4-diamine, 2-(aminomethyl)benzene-1,4-diamine, 2-(2,5-diaminophenoxy)ethanol, N-[2-(2,5-diaminophenoxy)ethyl]-acetamide, N,N-dimethylbenzene-1,4-diamine, N,N-diethylbenzene-1,4-diamine, N,N-dipropylbenzene-1,4-diamine, 2-[(4-aminophenyl)(ethyl)amino]ethanol, 2-[(4-amino-3-methyl-phenyl)-(2-hydroxy-ethyl)-amino]-ethanol, N-(2-methoxyethyl)-benzene-1,4-diamine, 3-[(4-aminophenyl)amino]propan-1-ol, 3-[(4-aminophenyl)-amino]propane-1,2-diol, N-[4-[(4-aminophenyl)amino]butyl]benzene-1,4-diamine, and 2-[2-(2-{2-[(2,5-diaminophenyl)-oxy]ethoxy}ethoxy)ethoxy]benzene. 1,3-bis(N-(2-hydroxyethyl)-N-(4-aminophenyl)amino)-2-propanol; 2,2'-[1,2-Ethanediyl-bis(oxy-2,1-ethanediyloxy)]-bis-benzene-1,4-diamine, and N,N-bis(2-hydroxyethyl)-1,4-phenylenediamine, as well as the water-soluble salts thereof.

Another category of oxidative dye precursors that can be used in the disclosed colorant systems includes 4-aminophenol and derivatives thereof. Non-limiting examples include 4-amino-phenol (commonly known as p-aminophenol), 4-methylamino-phenol, 4-amino-3-methyl-phenol, 4-amino-2-hydroxymethyl-phenol, 4-amino-2-methyl-phenol, 4-amino-1-hydroxy-2-(2'-hydroxyethylaminomethyl)benzene, 4-amino-2-methoxymethylphenol, 5-amino-2-hydroxy-benzoic acid, 1-(5-amino-2-hydroxy-phenyl)-ethane-1,2-diol, 4-amino-2-(2-hydroxy-ethyl)-phenol, 4-amino-3-(hydroxymethyl)phenol, 4-amino-3-fluorophenol, 4-amino-2-(aminomethyl)-phenol, 4-amino-2-fluoro-phenol; 1-hydroxy-2,4-diaminobenzene; 1-(2'-hydroxyethyloxy)-2,4-diaminobenzene; and 2,4-diamino-5-methylphenetol, as well as the water-soluble salts thereof.

A further category of oxidative dye precursors that can be used in the disclosed colorant systems includes 2-aminophenol and derivatives thereof. Non-limiting examples include 2-amino-phenol (commonly known as o-aminophenol), 2,4-diaminophenol, 2-amino-5-methyl-phenol, 2-amino-6-methyl-phenol, N-(4-amino-3-hydroxyphenyl)acetamide, and 2-amino-4-methylphenol, as well as the water-soluble salts thereof.

A yet further category of oxidative dye precursors that can be used in the disclosed colorant systems includes pyrazole and derivatives thereof. Non-limiting examples include pyrazole, 1-hydroxyethyl-4,5-diaminopyrazole, 3,4-diamino-5-hydroxypyrazole, 3,5-diaminopyrazole, 3,5-diamino pyrazol-1-carboxamide, 3-amino-5-hydroxypyrazole, 1-phenyl-2-methylpyrazole, 1-phenyl-3-methylpyrazole-5-one, 3,5-dimethylpyrazole, 3,5-dimethylpyrazole-1-methanol, 1-methyl-4,5-diaminopyrazole, 1-methylethyl-4,5-diaminopyrazole, 1-phenylmethyl-4,5-diaminopyrazole, 1-methyl-4,5-diaminopyrazole, 1-(4-methylphenyl)methyl-4,5-diaminopyrazole, and 1-methyl-3-phenyl-4,5-diaminopyrazole, as well as the water-soluble salts thereof.

A still yet further category of oxidative dye precursors that can be used in the disclosed colorant systems includes pyrimidines and derivatives thereof. One non-limiting example are the tetraminopyrimidines, inter alia, 2,4,5,6-tetraminopyrimidine and the lower alkyl derivatives thereof. A further example includes the triaminohydroxypyrimidines, inter alia, 4-hydroxy-2,5,6-triaminopyrimidine, 2-hydroxy-4,5,6-triaminopyrimidine and 5-hydroxy-2,4,6-triaminopyrimidine. Another example includes mono- and diamino dihydroxypyrimidines, inter alia, 2,6-dihydroxy-4,5-diaminopyrimidine, 2,4-diamino-6-hydroxy-pyrimidine and 4,6-dihydroxy-2,5-diaminopyrimidine. Included in this category are the water soluble salts of pyrimidines.

The disclosed compositions can further comprise one or more cationic indazoline thiazolazo dyes as disclosed in U.S. Patent Application Publication 2009/0034510 A1 the disclosure of which is included herein by reference in its entirety. The disclosed compositions can also comprise one or more 4,5-diaminoprazoles as disclosed in U.S. Pat. No. 6,554,871 the disclosure of which is included herein by reference in its entirety.

Coupling Agents

In one aspect the disclosed keratin-comprising fiber dyeing compositions comprise one or more coupling agents. Non-limiting examples of suitable coupling agents include, resorcinol, 2-methyl resorcinol, 4-amino-2-methylphenol, 4-chlororesorcinol, 2-amino-4-chlorophenol, 2-amino-4-chlorophenol, 5-amino-4-methoxy-2-methylphenol, 3-aminophenol, 1-methyl-2-hydroxy-4-aminobenzene, 3-N,N-dimethyl aminophenol, 2,6-dihydroxy-3,5-dimethoxypyridine, 5-amino-3-methylphenol, 6-amino-3-methylphenol, 3-amino-2-methylamino-6-methoxypyridine, 2-amino-3-hydroxy-pyridine, 2-dimethyl-amino-5-aminopyridine, 2,6-diaminopyridine, 1,3-diamino-benzene, 1-amino-3-(2'-hydroxyethylamino)benzene, 1-amino-3-[bis(2'-hydroxyethyl)amino]benzene, 1-naphthol, 4,6-dichlororesorcinol, 1,3-diamino-toluene, 1-hydroxy naphthalene, 4-hydroxy-1,2-methylenedioxy benzene, 1,5-dihydroxy naphthalene, 1,6-dihydroxy naphthalene, 1,7-dihydroxy naphthalene, 2,7-dihydroxy naphthalene, 1-hydroxy-2-methyl naphthalene, 4-hydroxy-1,2-methyldioxy benzene, 2,4-diamino-3-chlorophenol, 2,6-dihydroxyethylamino toluene, 5-amino-2-methoxyphenol and 1-methoxy-2-amino-4-(2'-hydroxyethyl amino)benzene, or the water-soluble salts thereof.

In one embodiment, the compositions comprise coupling agents chosen from 2,6-dihydroxy-ethylamino toluene, 2-methyl resorcinol, 4-amino-2-methylphenol and 1-naphthol.

The disclosed compositions can further comprise one or more couplers as disclosed in U.S. Pat. No. 5,529,583, the disclosure of which is included herein by reference in its entirety.

Red Hair Colorant Systems

One aspect of the disclosed compositions relates to colorant systems comprising a combination of one or more precursors useful for providing a red color, tint, or hue to keratin-containing fibers. In one embodiment the colorant precursor composition comprises:

a) from about 0.5% to about 25% by weight of 1,4-phenylenediamine;

b) from about 0.5% to about 25% by weight of 4-aminophenol;

c) from about 5% to about 65% by weight of 4-amino-2-hydroxyphenol;

d) from about 2.5% to about 40% by weight of 2-nitro-N-(2-hydroxyethyl)aniline;

e) from about 5% to about 65% by weight of 4-(3-hydroxypropylamino)-3-nitrophenol; and f) from about 5% to about 65% by weight of 1-hydroxyethyl-4,5-diamino pyrazole sulfate.

When a composition according to the present disclosure comprises this embodiment of the colorant system the composition can comprise from about 0.15% to about 3% by weight of the colorant system. In one embodiment, the composition can comprise from about 0.3% to about 2.5% by weight of this iteration of the colorant system. In another embodiment, the composition can comprise from about 0.37% to about 1.9% by weight of this iteration of the colorant system.

In another embodiment the colorant precursor composition comprises:
a) from about 1% to about 20% by weight of 1,4-phenylenediamine;
b) from about 5% to about 55% by weight of 4-aminophenol;
c) from about 10% to about 65% by weight of 4-amino-2-hydroxytoluene;
d) from about 5% to about 55% by weight of 4-(3-hydroxypropylamino)-3-nitrophenol; and
e) from about 5% to about 55% by weight of 4-amino-3-nitrophenol.

When a composition according to the present disclosure comprises this embodiment of the colorant system the composition can comprise from about 0.2% to about 3% by weight of the composition. In one embodiment, the composition can comprise from about 0.4% to about 2.5% by weight of this iteration of the colorant system. In another embodiment, the composition can comprise from about 0.52% to about 2.1% by weight of this iteration of the colorant system.

In a further embodiment the colorant precursor composition comprises:
a) from about 1% to about 45% by weight of 1,4-phenylenediamine;
b) from about 1% to about 60% by weight of 4-aminophenol;
c) from about 8% to about 80% by weight of 4-amino-2-hydroxytoluene;
d) from about 0.5% to about 25% by weight of 2-nitro-N-(2-hydroxyethyl)aniline; and
e) from about 5% to about 65% by weight of 4-(3-hydroxypropylamino)-3-nitrophenol.

When a composition according to the present disclosure comprises this embodiment of the colorant system the composition can comprise from about 0.2% to about 4% by weight of the composition. In one embodiment, the composition can comprise from about 0.4% to about 3.5% by weight of this iteration of the colorant system. In another embodiment, the composition can comprise from about 0.53% to about 2.75% by weight of this iteration of the colorant system.

The following are non-limiting examples of compositions that can serve as colorant systems suitable for use in providing a red color, hue or tint to keratin-containing fibers.

TABLE I

EXAMPLES OF COLORANT COMPOSITIONS (weight %)

| Precursor | 1 | 2 | 3 | 4 | 5 |
|---|---|---|---|---|---|
| 1,4-phenylenediamine | 4.9 | 4.8 | 4.6 | 4.8 | 4.8 |
| 4-aminophenol | 3.3 | 3.3 | 3.6 | 3.6 | 3 |
| 4-amino-2-hydroxytoluene | 32.8 | 32.9 | 32.9 | 32.9 | 32.9 |
| 2-nitro-N-(2-hydroxyethyl)aniline (HC Yellow 2) | 10.9 | 10.9 | 10.9 | 10.9 | 10.9 |
| 4-(3-hydroxypropylamino)-3-nitrophenol | 15.3 | 15.3 | 15 | 14.2 | 14 |
| 1-hydroxyethyl-4,5-diamino pyrazole sulfate | 32.8 | 32.8 | 32.8 | 32.8 | 32.8 |

TABLE II

EXAMPLES OF COLORANT COMPOSITIONS (weight %)

| Precursor | 6 | 7 | 8 | 9 | 10 |
|---|---|---|---|---|---|
| 1,4-phenylenediamine | 4 | 4.2 | 3.8 | 4.2 | 4 |
| 4-aminophenol | 23.9 | 26.2 | 20.9 | 20.9 | 20.9 |
| 4-amino-2-hydroxytoluene | 37.7 | 33.7 | 37.7 | 37.7 | 37.7 |
| 4-(3-hydroxypropylamino)-3-nitrophenol | 16.7 | 14.9 | 16.7 | 15 | 15.6 |
| 4-amino-3-nitrophenol | 20.9 | 21.0 | 20.9 | 20.2 | 20.7 |

TABLE III

EXAMPLES OF COLORANT COMPOSITIONS (weight %)

| Precursor | 11 | 12 | 13 | 14 | 15 |
|---|---|---|---|---|---|
| 1,4-phenylenediamine | 9.4 | 9.4 | 9.4 | 9.4 | 9.4 |
| 4-aminophenol | 20.0 | 21.0 | 21.0 | 20.5 | 21.0 |
| 4-amino-2-hydroxytoluene | 35.9 | 35.1 | 37.1 | 35.3 | 35.1 |
| 2-nitro-N-(2-hydroxyethyl)aniline (HC Yellow 2) | 5.1 | 5.3 | 5.3 | 5.4 | 5.3 |
| 4-(3-hydroxypropylamino)-3-nitrophenol | 29.2 | 28.8 | 29.2 | 29.4 | 29.2 |

Brown Hair Colorant Systems

One aspect of the disclosed compositions relates to colorant systems comprising a combination of one or more precursors useful for providing a brown color, tint, or hue to keratin-containing fibers. In one embodiment the colorant precursor composition comprises:
a) from about 7% to about 75% by weight of 1,4-phenylenediamine;
b) from about 2% to about 55% by weight of 4-aminophenol;
c) from about 2% to about 55% by weight of 3-aminophenol;
d) from about 2% to about 55% by weight of 1,3-dihydroxybenzene; and
e) from about 2% to about 55% by weight of 4-chloro-1,3-dihydroxybenzene.

When a composition according to the present disclosure comprises this embodiment of the colorant system the composition can comprise from about 0.2% to about 5% by weight of the composition. In one embodiment, the composition can comprise from about 0.5% to about 4% by weight of this iteration of the colorant system. In another embodiment, the composition can comprise from about 0.6% to about 3% by weight of this iteration of the colorant system.

In another embodiment, the colorant precursor composition comprises:
a) from about 5% to about 35% by weight of 1,4-phenylenediamine;
b) from about 10% to about 80% by weight of 4-aminophenol;
c) from about 10% to about 80% by weight of 1,3-dihydroxybenzene;
d) from about 0.5% to about 20% by weight of 2-nitro-N-(2-hydroxyethyl)aniline; and
e) from about 0.5% to about 20% by weight of 1-naphthol.

When a composition according to the present disclosure comprises this embodiment of the colorant system the composition can comprise from about 0.2% to about 3% by weight of the composition. In one embodiment, the composition can comprise from about 0.4% to about 2.5% by weight of this iteration of the colorant system. In another embodiment, the composition can comprise from about 0.27% to about 1.4% by weight of this iteration of the colorant system.

In a further embodiment, the colorant precursor composition comprises:
 a) from about 10% to about 70% by weight of 1,4-phenylenediamine;
 b) from about 3% to about 25% by weight of 4-aminophenol;
 c) from about 5% to about 25% by weight of 3-aminophenol;
 d) from about 5% to about 25% by weight of 3-aminophenol; and
 e) from about 5% to about 15% by weight of 1-hydroxy-4-(4-methylanilino)anthracene-9,10-dione (DC violet 2).

When a composition according to the present disclosure comprises this embodiment of the colorant system the composition can comprise from about 0.1% to about 2.5% by weight of the composition. In one embodiment, the composition can comprise from about 0.25% to about 1.75% by weight of this iteration of the colorant system. In another embodiment, the composition can comprise from about 0.5% to about 1.5% by weight of this iteration of the colorant system.

The following are non-limiting examples of compositions that can serve as colorant systems suitable for use in providing a brown color, hue or tint to keratin-containing fibers.

TABLE IV

EXAMPLES OF COLORANT COMPOSITIONS (weight %)

| Precursor | 16 | 17 | 18 | 19 | 20 |
|---|---|---|---|---|---|
| 1,4-phenylenediamine | 36.5 | 37.7 | 37.7 | 37.7 | 32.2 |
| 4-aminophenol | 18.7 | 15.7 | 15.7 | 15.7 | 15.7 |
| 3-aminophenol | 12.2 | 19.2 | 12.2 | 12.2 | 12.2 |
| 1,3-dihydroxybenzene | 12.6 | 10.6 | 12.6 | 12.6 | 12.6 |
| 4-chloro-1,3-dihydroxybenzene | 20.8 | 21.2 | 20.8 | 20.8 | 24.8 |

TABLE V

EXAMPLES OF COLORANT COMPOSITIONS (weight %)

| Precursor | 21 | 22 | 23 | 24 | 25 |
|---|---|---|---|---|---|
| 1,4-phenylenediamine | 21.9 | 21.1 | 22.5 | 21.6 | 21.8 |
| 4-aminophenol | 37.2 | 38.2 | 37.5 | 38.2 | 38.2 |
| 1,3-dihydroxybenzene | 33.8 | 33.6 | 33.0 | 32.6 | 33.2 |
| 2-nitro-N-(2-hydroxyethyl)aniline | 3.0 | 1.5 | 1.5 | 2.0 | 1.5 |
| 1-naphthol | 5.0 | 5.5 | 5.5 | 5.1 | 5.4 |

TABLE VI

EXAMPLES OF COLORANT COMPOSITIONS (weight %)

| Precursor | 26 | 27 | 28 | 29 | 30 |
|---|---|---|---|---|---|
| 1,4-phenylenediamine | 38.8 | 37.2 | 39.7 | 39.7 | 39.7 |
| 4-aminophenol | 8.7 | 8.5 | 8.9 | 8.9 | 8.9 |
| 3-aminophenol | 6.2 | 6.2 | 6.2 | 6.2 | 6.2 |
| 1,3-dihydroxybenzene | 39.7 | 39.7 | 39.7 | 39.7 | 39.7 |
| 1-hydroxy-4-(4-methylanilino)-anthracene-9,10-dione (DC violet 2) | 3.4 | 3.4 | 4.0 | 3.4 | 3.4 |
| N,N-bis(2-hydroxyethyl)-1,4-phenylenediamine | 2.1 | 2.1 | 2.1 | 2.1 | 2.1 |

One aspect of the disclosed compositions relates to colorant systems comprising a combination of one or more precursors useful for providing a blonde color, tint, or hue to keratin-containing fibers. In one embodiment the colorant precursor composition comprises:
 a) from about 10% to about 70% by weight of 1,4-phenylenediamine;
 b) from about 10% to about 70% by weight of 4-aminophenol;
 c) from about 1% to about 35% by weight of 1,3-dihydroxybenzene;
 d) from about 1% to about 35% by weight of 4-chloro-1,3-dihydroxybenzene;
 e) from about 0.5% to about 35% by weight of 1-hydroxy-4-(4-methylanilino)anthracene-9,10-dione; and
 f) from about 0.5% to about 20% by weight of N,N-bis(2-hydroxyethyl)-1,4-phenylenediamine.

When a composition according to the present disclosure comprises this embodiment of the colorant system the composition can comprise from about 0.15% to about 3% by weight of the composition. In one embodiment, the composition can comprise from about 0.3% to about 2.5% by weight of this iteration of the colorant system. In another embodiment, the composition can comprise from about 0.3% to about 0.5% by weight of this iteration of the colorant system.

In another embodiment the colorant precursor composition comprises:
 a) from about 3% to about 75% by weight of 1,4-phenylenediamine;
 b) from about 2% to about 50% by weight of 4-aminophenol;
 c) from about 2% to about 60% by weight of 4-chloro-1,3-dihydroxybenzene;
 d) from about 2% to about 60% by weight of 2-methyl-1,3-dihydroxybenzene;
 e) from about 2% to about 50% by weight of N,N-bis(2-hydroxyethyl)-1,4-phenylenediamine; and
 f) from about 0.1% to about 20% by weight of 1-hydroxy-4-(4-methylanilino)anthracene-9,10-dione.

When a composition according to the present disclosure comprises this embodiment of the colorant system the composition can comprise from about 0.05% to about 3% by weight of the composition. In one embodiment, the composition can comprise from about 0.075% to about 1% by weight of this iteration of the colorant system. In another embodiment, the composition can comprise from about 0.09% to about 0.3% by weight of this iteration of the colorant system.

In a further embodiment the colorant precursor composition comprises:
 a) from about 2% to about 35% by weight of 1,4-phenylenediamine;
 b) from about 2% to about 30% by weight of 4-aminophenol;
 c) from about 15% to about 80% by weight of 1,3-dihydroxybenzene;
 d) from about 0.5% to about 15% by weight of 2-nitro-N-(2-hydroxyethyl)aniline; and
 e) from about 2% to about 55% by weight of 1-naphthol.

When a composition according to the present disclosure comprises this embodiment of the colorant system the composition can comprise from about 0.2% to about 4% by weight of the composition. In one embodiment, the composition can comprise from about 0.4% to about 3.5% by weight of this iteration of the colorant system. In another embodiment, the composition can comprise from about 0.75% to about 1.3% by weight of this iteration of the colorant system.

The following are non-limiting examples of compositions that can serve as colorant systems suitable for use in providing a red color, hue or tint to keratin-containing fibers.

TABLE VII

EXAMPLES OF COLORANT COMPOSITIONS (weight %)

| Precursor | 31 | 32 | 33 | 34 | 35 |
|---|---|---|---|---|---|
| 1,4-phenylenediamine | 37.2 | 35.9 | 37.8 | 37.8 | 37.8 |
| 4-aminophenol | 34.4 | 34.4 | 30.2 | 30.2 | 30.2 |
| 1,3-dihydroxybenzene | 10.6 | 10.6 | 10.6 | 10.6 | 10.6 |
| 4-chloro-1,3-dihydroxybenzene | 14.9 | 15.0 | 15.1 | 15.1 | 15.3 |
| 1-hydroxy-4-(4-methylanilino)-anthracene-9,10-dione (DC violet 2) | 2.5 | 2.5 | 2.5 | 2.5 | 2.5 |
| N,N-bis(2-hydroxyethyl)-1,4-phenylenediamine | 3.9 | 3.5 | 3.8 | 3.8 | 3.8 |

TABLE VIII

EXAMPLES OF COLORANT COMPOSITIONS (weight %)

| Precursor | 36 | 37 | 38 | 39 | 40 |
|---|---|---|---|---|---|
| 1,4-phenylenediamine | 40.7 | 44.1 | 43.3 | 40.5 | 40.5 |
| 4-aminophenol | 11.1 | 12.0 | 11.1 | 11.1 | 11.1 |
| 4-chloro-1,3-dihydroxybenzene | 16.3 | 10.2 | 13.8 | 16.3 | 16.3 |
| 2-methyl-1,3-dihydroxybenzene | 14.9 | 14.9 | 14.9 | 14.9 | 14.9 |
| N,N-bis(2-hydroxyethyl)-1,4-phenylenediamine | 11.1 | 11.1 | 11.1 | 14.1 | 11.1 |
| 1-hydroxy-4-(4-methylanilino)-anthracene-9,10-dione (DC violet 2) | 5.9 | 5.9 | 5.9 | 5.9 | 6.0 |

TABLE IX

EXAMPLES OF COLORANT COMPOSITIONS (weight %)

| Precursor | 41 | 42 | 43 | 44 | 45 |
|---|---|---|---|---|---|
| 1,4-phenylenediamine | 8.0 | 8.4 | 8.4 | 8.4 | 8.0 |
| 4-aminophenol | 40.0 | 52.0 | 48.0 | 48.0 | 52.0 |
| 1,3-dihydroxybenzene | 36.6 | 36.9 | 37.6 | 37.6 | 37.4 |
| 2-nitro-N-(2-hydroxyethyl)aniline (HC Yellow 2) | 1.0 | 1.0 | 1.0 | 1.0 | 1.0 |
| 1-naphthol | 3.9 | 5.0 | 5.0 | 5.0 | 5.0 |

Black Hair Colorant Systems

One aspect of the disclosed compositions relates to colorant systems comprising a combination of one or more precursors useful for providing a black color, tint, or hue to keratin-containing fibers. In one embodiment the colorant precursor composition comprises:
 a) from about 10% to about 70% by weight of 1,4-phenylenediamine;
 b) from about 1% to about 35% by weight of 1,3-dihydroxybenzene;
 c) from about 1% to about 35% by weight of 2,4-diaminophenoxyethanol sulfate;
 d) from about 0.5% to about 35% by weight of 3-aminophenol; and
 e) from about 0.5% to about 20% by weight of N,N-bis(2-hydroxyethyl)-1,4-phenylenediamine.

When a composition according to the present disclosure comprises this embodiment of the colorant system the composition can comprise from about 0.15% to about 7% by weight of the composition. In one embodiment, the composition can comprise from about 0.5% to about 5% by weight of this iteration of the colorant system. In another embodiment, the composition can comprise from about 2% to about 5% by weight of this iteration of the colorant system.

The following are non-limiting examples of compositions that can serve as colorant systems suitable for use in providing a red color, hue or tint to keratin-containing fibers.

TABLE X

EXAMPLES OF COLORANT COMPOSITIONS (weight %)

| Precursor | 46 | 47 | 48 | 48 | 50 |
|---|---|---|---|---|---|
| 1,4-phenylenediamine | 46.2 | 45 | 46.1 | 47.2 | 46 |
| 1,3-dihydroxybenzene | 21.5 | 23.6 | 22 | 21.5 | 21.5 |
| 2,4-diaminophenoxyethanol sulfate | 7.7 | 8 | 7.7 | 7.2 | 7.8 |
| 3-aminophenol | 16.9 | 16.9 | 16.7 | 16.9 | 16.9 |
| N,N-bis(2-hydroxyethyl)-1,4-phenylenediamine sulfate | 7.7 | 6.5 | 7.5 | 7.2 | 7.8 |

TABLE XI

EXAMPLES OF COLORANT COMPOSITIONS (weight %)

| Precursor | 51 | 52 | 53 | 54 | 55 |
|---|---|---|---|---|---|
| 1,4-phenylenediamine | 44.2 | 44.2 | 44.2 | 45.8 | 45.8 |
| 1,3-dihydroxybenzene | 23.2 | 23.2 | 20.8 | 20.8 | 23.6 |
| 2,4-diaminophenoxyethanol sulfate | 7.9 | 8 | 9.2 | 8.3 | 6.9 |
| 3-aminophenol | 16.8 | 16.6 | 16.8 | 16.8 | 16.8 |
| N,N-bis(2-hydroxyethyl)-1,4-phenylenediamine sulfate | 7.9 | 8 | 9.2 | 8.3 | 6.9 |

TABLE XII

EXAMPLES OF COLORANT COMPOSITIONS (weight %)

| Precursor | 56 | 57 | 58 | 59 | 60 |
|---|---|---|---|---|---|
| 1,4-phenylenediamine | 44.4 | 44.6 | 46.2 | 46.3 | 50 |
| 1,3-dihydroxybenzene | 23.2 | 23.4 | 21.3 | 21.1 | 20 |
| 2,4-diaminophenoxyethanol sulfate | 7.8 | 7.7 | 7.8 | 7.7 | 7.8 |
| 3-aminophenol | 16.8 | 16.6 | 16.9 | 17.2 | 14.4 |
| N,N-bis(2-hydroxyethyl)-1,4-phenylenediamine sulfate | 7.8 | 7.7 | 7.8 | 7.7 | 7.8 |

The disclosed compositions comprise one or more optional ingredients, however, the compositions comprise at least one ingredient from any listing of optional ingredients. In addition, any of the herein below recited ingredients can be specifically excluded from any of the disclosed compositions, for example, an individual emollient can be excluded or emollients as a class can be excluded from any of the compositions falling under the disclosure or the compositions, methods or kits recited in the appended claims.

Enhancement Ingredients

Detangling Agent

The disclosed colorant compositions can comprise one or more detangling agents chosen from $C_{10}$-$C_{22}$ alkyl esters of alkoxylated trimethylolpropane, $C_{10}$-$C_{22}$ alkenyl mono-ene esters of alkoxylated trimethylolpropane, $C_{10}$-$C_{22}$ alkynyl mono-yne esters of alkoxylated trimethylolpropane, and mixtures thereof can have the formula:

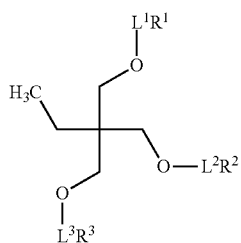

wherein $R^1$, $R^2$ and $R^3$ are each independently chosen from:
  i) hydrogen;
  ii) $C_{10}$-$C_{22}$ carboxyalkyl;
  iii) $C_{10}$-$C_{22}$ carboxyalkenyl; and
  iv) $C_{10}$-$C_{22}$ carboxyalkynyl;

$L^1$, $L^2$ and $L^3$ are linking units each independently chosen from:
  i) —$(CR^{4a}R^{4b})_w$O—; and
  ii) —$[(CR^{5a}R^{5b})_w]_x[O(CR^{6a}R^{6b})_y]_z$O—;

the index w is from 2 to 150, the index x is from 1 to 50, the index y is from 3 to 300, the index z is from 1 to 20; and $R^{4a}$, $R^{4b}$, $R^{5a}$, $R^{5b}$, $R^{6a}$, and $R^{6b}$ are each independently chosen from:
  i) hydrogen; and
  ii) methyl.

The $R^1$, $R^2$ and $R^3$ units comprise $C_{10}$-$C_{22}$ fatty acid residues of the corresponding $C_{10}$-$C_{22}$ fatty acids. In a one aspect of the disclosed detangling agents, $R^1$, $R^2$ and $R^3$ are from 90% to about 99.9% by weight of a single $C_{10}$-$C_{22}$ carboxyalkenyl units. Non-limiting examples of $R^1$, $R^2$ and $R^3$ according to this aspect include the following cis-D carboxyalkenyl residues:
  i) —C(O)(CH)$_7$CH═CH(CH$_2$)$_3$CH$_3$ (myristoleoyl);
  ii) —C(O)(CH)$_7$CH═CH(CH$_2$)$_5$CH$_3$ (palmitoleoyl);
  iii) —C(O)(CH)$_4$CH═CH(CH$_2$)$_8$CH$_3$ (sapienoyl);
  iv) —C(O)(CH)$_7$CH═CH(CH$_2$)$_7$CH$_3$ (oleoyl);
  v) —C(O)(CH)$_7$CH═CHCH$_2$(CH$_2$)$_4$CH$_3$ (linoleoyl); and
  vi) —C(O)(CH)$_{11}$CH═CH(CH$_2$)$_7$CH$_3$ (erucoyl).

In another aspect of the disclosed detangling agents, $R^1$, $R^2$ and $R^3$ are from 90% to about 99.9% by weight of a mixture of $C_{10}$-$C_{22}$ carboxyalkenyl units. Non-limiting examples of $R^1$, $R^2$ and $R^3$ according to this aspect include the following cis-D carboxyalkenyl residues:
  i) —C(O)(CH)$_7$CH═CH(CH$_2$)$_3$CH$_3$ (myristoleoyl);
  ii) —C(O)(CH)$_7$CH═CH(CH$_2$)$_5$CH$_3$ (palmitoleoyl);
  iii) —C(O)(CH)$_4$CH═CH(CH$_2$)$_8$CH$_3$ (sapienoyl);
  iv) —C(O)(CH)$_7$CH═CH(CH$_2$)$_7$CH$_3$ (oleoyl);
  v) —C(O)(CH)$_7$CH═CHCH$_2$(CH$_2$)$_4$CH$_3$ (linoleoyl); and
  vi) —C(O)(CH)$_{11}$CH═CH(CH$_2$)$_7$CH$_3$ (erucoyl).

The first aspect of $L^1$, $L^2$ and $L^3$ relates to linking units that comprise polyoxyethylene polyoxypropylene residues that are derived from the random co-polymerization of ethylene oxide and propylene oxide. The $L^1$, $L^2$ and $L^3$ units can be attached to the central trimethylolpropane core by either grafting the $L^1$, $L^2$ and $L^3$ units onto the trimethylolpropane core or by reacting a polyoxyethylene polyoxypropylene precursor with the trimethylolpropane core.

A one embodiment of this aspect includes a detangling agent wherein each of $L^1$, $L^2$ and $L^3$ comprises greater than about 90% by weight of a polyoxyethylene polyoxypropylene residue comprising about 120 polyoxyethylene and 10 polyoxypropylene units (PEF/PPG 120/10) represented by the formula:

—[(CH$_2$CH$_2$)]$_{120}$[O(CH$_2$CH$_2$)$_3$]$_{10}$O—.

Non-limiting examples of detangling agents according to this embodiment include PEG/PPG-120/10 trimethylolpropane trioleate (and) laueth-2 [CAS Reg. No. 37339-03-0] available as an admixture with ethoxylated lauryl alcohol from Cognis as Arylpon™ TT.

UV Radiation Absorbers

The disclosed compositions can comprise from about 0.005% to 0.05% by weight of one or more UV absorbers. This includes the disclosed colorant systems, as well as the disclosed activator compositions. In one aspect the compositions comprise from about 0.01% to about 0.04% by weight of one or more UV absorbers. The following are non-limiting examples of UV absorbers ethylhexyl methoxycinnamate (octyl methoxycinnamate), methoxydibenzoylmethane (i.e., Parsol™ 1789, Eusolex™ 9020 and Escalol™ 517), polyoxypropylene, polyoxyethylene ethers of aliphatic alcohols (for example, PPG-26 Buteth-26), ethylhexyl salicylate, and polyoxyethylene derivatives of hydroxy fatty acid containing fats and oils, (for example, PEG-40 hydrogenated castor oil).

Conditioning Agents

Keratin-containing fibers can become dry and brittle due to exposure to UV radiation, chemicals used for cleaning the fibers, and from the wearing of apparel. In one embodiment, the disclosed compositions can comprise from about 0.1% to about 1.5% by weight of one or more conditioning agents.

The conditioning agents can comprise polymeric materials or small naturally occurring molecules that interact with the keratin-containing fiber to provide a benefit to the properties of the fibers. In one aspect, the disclosed compositions comprise one or more nonionic amphiphilic homopolymers or copolymers. In one embodiment, the compositions comprise polyalkylene glycols having the formula:

HO(CH$_2$CH$_2$O)$_x$H wherein the index x represent the average number of ethyleneoxy units in the glycol polymer. The index x can be represented by a whole number or a fraction. For example, a polyethylene glycol having an average molecular weight of 8,000 g/mole (PEG 8000) can be equally represented by the formulae:

HO(CH$_2$CH$_2$O)$_{181}$H or HO(CH$_2$CH$_2$O)$_{181.4}$H or the polyethylene glycol can be represented by the common short hand notation: PEG 8000. This notation, common to the artisan is used interchangeably throughout the specification to indicate polyethylene glycols and their average molecular weight. The formulator will understand that depending upon the source of the polyethylene glycol, the range of molecular weights found within a particular sample or lot can range over more or less values of x. For example, one source of PEG 8000 can include polymers wherein the value of x can be from about 175 to about 187, whereas another source can report the range of molecular weights such that x can be from about 177 to about 184. In fact, the formulator, depending upon the condition of the user's keratin-containing fibers, can provide a conditioner system that comprises an admixture of different polyethylene glycols in varying amounts. For example, from about 0.5% by weight of the colorant system can comprise PEG 4000 and 0.5% by weight of the colorant system can comprise PEG 8000.

One non-limiting example of a suitable conditioning agent includes polyethylene glycols having an average molecular weight from about 1200 g/mol to about 20,000 g/mol. A further example of a suitable conditioning agent includes the polyethylene glycols having an average molecular weight from about 3,000 g/mol to about 12,000 g/mol. Another example of a suitable conditioning agent includes the polyethylene glycols having an average molecular weight from about 4,000 g/mol to about 10,000 g/mol. One non-limiting example of a suitable conditioning agent is a polyethylene glycol having an average molecular weight of about 8,000 g/mol, for example, PEG 8000.

Another embodiment of conditioning agents relates to polypropylene glycols having the formula:

HO[CH(CH$_3$)CH$_2$O]$_x$H wherein the index x represent the average number of propyleneoxy units in the glycol polymer. As in the case of ethylene glycols, for propylene glycols the index x can be represented by a whole number or a fraction. For example, a polypropylene glycol having an average molecular weight of 8,000 g/mole (PEG 8000) can be equally represented by the formulae:

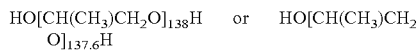

or the polypropylene glycol can be represented by the common, short hand notation: PPG 8000.

One non-limiting example of the disclosed conditioning agents includes polypropylene glycols having an average molecular weight from about 1200 g/mol to about 20,000 g/mol. A further example of the disclosed conditioning agents includes the polypropylene glycols having an average molecular weight from about 3,000 g/mol to about 12,000 g/mol. Another example of the disclosed conditioning agents includes the polypropylene glycols having an average molecular weight from about 4,000 g/mol to about 10,000 g/mol. One non-limiting example of the disclosed conditioning agents includes a polypropylene glycol having an average molecular weight of about 8,000 g/mol, for example, PER 8000.

Polypropylene glycols can be admixed with polyethylene glycols to form a conditioning agent system for use in the disclosed colorant systems.

A further example of conditioning agents includes poloxamers having the formula:

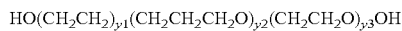

these are nonionic block copolymers composed of a polypropyleneoxy unit flanked by two polyethyleneoxy units. The indices $y^1$, $y^2$, and $y^3$ have values such that the poloxamer has an average molecular weight of from about 1000 g/mol to about 20,000 g/mol. These nonionic conditioning agents are also well known by the trade name PLURONICS™. These compounds are commonly named with the word Poloxamer followed by a number to indicate the specific co-polymer, for example Poloxamer 407 having two PEG blocks of about 101 units ($y^1$ and $y^3$ each equal to 101) and a polypropylene block of about 56 units. This extracellular desiccant is available from BASF under the trade name LUTROL™ F-17.

One iteration of this embodiment relates to colorant systems that comprise form about 0.1% to about 1.0% by weight of poloxamer 185 [CAS Reg. No. 9003-11-6] wherein the indices $y^1$, $y^2$, and $y^3$ have the average values of 19, 30 and 10 respectively.

In another aspect, the disclosed compositions can comprise a colorant system comprising lysine as a conditioning agent. The disclosed compositions can comprise from about 0.0001% to about 1% by weight of lysine. In one aspect, the compositions comprise from about 0.005% to about 0.5% by weight of lysine.

In a further embodiment, the colorant systems that comprise the disclosed compositions can comprise an admixture of lysine and a nonionic amphiphilic polymer. A non-limiting example includes colorant systems comprising:

i) from about 0.005% to about 0.5% by weight of lysine; and
ii) from about 0.1% to about 1.0% by weight of poloxamer 185.

Adjunct Ingredients

In addition to the disclosed color precursors, detangling agents, UV radiation absorbers, and lysine, the disclosed compositions can further comprise one or more adjunct ingredients. Non-limiting examples of adjunct ingredients include moisturizers, chelating agents, anti-oxidation agents, pH adjusters, emulsifiers, shine agents, solubilizers, fragrances, pearlizers, and the like.

Emollients

The disclosed compositions can comprise from about 0.1% to about 3% by weight of one or more emollients. Non-limiting examples of emollients include but are not limited to $C_{14}$-$C_{22}$ fatty alcohols, for example, cetyl alcohol, stearyl alcohol, cetearyl alcohol; $C_{14}$-$C_{22}$ fatty alcohols fatty acid esters, for example, isopropyl mysristate, isopropyl palmitate, diisopropyl dimer dilinoleate; $C_8$-$C_{14}$ fatty alcohol triglycerides, for example, caprylic/capric triglyceride; cetyl esters; $C_8$-$C_{40}$ hydrocarbons, for example, light mineral oil, white petrolatum; and waxes, for example, beeswax. Mixtures of one or more classes of emollients can also comprise the disclosed compositions, for example, a mixture of $C_{14}$-$C_{22}$ fatty alcohols and $C_{14}$-$C_{22}$ fatty alcohols fatty acid esters.

Emulsifiers

The disclosed compositions can further comprise from about 5% to about 25% by weight of one or more emulsifiers.

Non-limiting examples of emulsifiers include $C_{14}$-$C_{22}$ fatty alcohols chosen from 1-tetradecanol (myristyl alcohol), 1-hexadecanol (cetyl alcohol), cis-9-hexadecen-1-ol (plamitoleyl alcohol), 1-octadecanol (stearyl alcohol), cis-9-octadecen-1-ol (oleyl alcohol), trans-9-octadecen-1-ol (elaidyl alcohol), 1-eicosanol (arachidyl alcohol), and 1-docosanol (behenyl alcohol). Further non-limiting examples of emulsifiers include esters of $C_{14}$-$C_{22}$ fatty alcohols and inorganic acids chosen from di-1-tetradecanyl phosphate (di-myristyl phosphate), di-1-hexadecanyl phosphate (di-cetyl phosphate), di-cis-9-hexadecen-1-yl phosphate (di-plamitoleyl phosphate), di-1-octadecanyl phosphate (di-stearyl phosphate), di-cis-9-octadecen-1-yl phosphate (di-oleyl phosphate), di-trans-9-octadecen-1-yl phosphate (di-elaidyl phosphate), di-1-eicosanyl phosphate (di-arachidyl phosphate), di-1-docosanyl phosphate (di-behenyl phosphate), 1-tetradecanyl sulfate (myristyl sulfate), 1-hexadecanyl sulfate (cetyl sulfate), cis-9-hexadecen-1-yl sulfate (plamitoleyl sulfate), 1-octadecanyl sulfate (stearyl sulfate), cis-9-octadecen-1-yl sulfate (oleyl sulfate), trans-9-octadecen-1-yl sulfate (elaidyl sulfate), 1-eicosanyl sulfate (arachidyl sulfate), and 1-docosanyl sulfate (behenyl sulfate).

Yet further non-limiting examples of emulsifiers include ethers of polyoxyethylene, polyoxypropylene, and polyoxyethylene/polyoxypropylene and inorganic acids or ethers of $C_{14}$-$C_{22}$ fatty alcohols chosen from PPG-5-Ceteth-20 phosphate, Ceteth-10 phosphate, Ceteth-10, and Ceteareth-20. Other suitable emulsifiers are phosphate esters, for example, cetearyl alcohol (and) dicetyl phosphate (and) ceteth-10 phosphate (available from Croda as CRODAFOSi™ CES) and cetyl PEG/PPG-10 1 dimethicone (methylpolysiloxane-225-cetylmethylpolysiloxane-225-poly(oxyethylene-225-oxypropylene) methylpolysiloxane copolymer). Still further non-limiting examples of emulsifiers includes non-ionic surfactants, for example, polysorbate 60, sorbitan monostearate, polyglyceryl-4 oleate, polyoxyethylene(4) lauryl ether, and the like. In certain embodiments, the emulsifier is chosen from poloxamers (e.g., PLURONIC™ F68, also known as POLOXAMER™ 188, a poly(ethylene glycol)-block-poly (propylene glycol)-block-poly(ethylene glycol), available from BASF, Ludwigshafen, Germany) and sorbitan trioleate (e.g., SPAN™ 85 available from Uniqema, New Castle, Del.).

Viscosity Control Agents

The disclosed compositions can comprises from about 2% to about 7% by weight of one or more viscosity control agents. The formulations of the present invention can also comprise a viscosity-enhancing agent. Examples of suitable viscosity enhancing agents include long chain alcohols, for example, cetyl alcohol, stearyl alcohol, cetearyl alcohol; cellulose ethers such as hydroxypropylmethylcellulose, hydroxyethylcellulose, hydroxypropylcellulose, and carboxymethylcellulose; polysaccharide gums such as xanthan gum; and homopolymers and copolymers of acrylic acid crosslinked with allyl sucrose or allyl pentaerythriol such as those polymers designated as carbomers in the United States Pharmacopoeia. Suitable carbomers include, for example, those available as CARBOPOL™ 934P, CARBOPOL™ 971P, CARBOPOL™ 940, CARBOPOL™ 974P, CARBOPOL™ 980, and PEMULEN™ TR-1 (USP/NF Monograph; Carbomer 1342), all available from Noveon, Cleveland, Ohio.

The activator composition can contain one or more thickeners that assist in maintaining an increased viscosity of the final composition resulting from mixture of the oxidative composition and the developer composition. This ensures that the mixture is of a sufficient viscosity to prevent it from dripping or running off the hair onto the user's face or the surrounding environment. Suitable thickeners are those set forth above with respect to the oxidative composition, and in the same ranges. Also suitable are a variety of water soluble anionic thickening polymers such as those disclosed in U.S. Pat. No. 4,240,450, which is hereby incorporated by reference in its entirety. In one aspect, the activator compositions comprise from about 0.01% to about 5% by weight of a thickener useful as a viscosity control agent. In one embodiment the activator composition comprises from about 0.05% to about 4% by weight of a thickener useful as a viscosity control agent. In a further embodiment the activator composition comprises from about 0.1% to about 3% by weight of a thickener useful as a viscosity control agent. Examples of such anionic polymers are copolymers of vinyl acetate and crotonic acid, graft copolymers of vinyl esters or acrylic or methacrylic acid esters, cross-linked graft copolymers resulting from the polymerization of at least one monomer of the ionic type, at least one monomer of the nonionic type, polyethylene glycol, and a crosslinking agent, and the like. Preferred are acrylate copolymers such as steareth-10 allyl ether acrylate copolymer.

Activator Compositions

The disclosed compositions useful for coloring keratin-containing fibers comprise an activator composition, comprising: comprise:
a) one or more catalysts;
b) optionally one or more active ingredients; and
c) optionally one or more diluents or carriers.
In one aspect, the activator compositions comprise:
a) from about 5% to about 20% by weight of one or more catalysts;
b) from about 3% to about 10% by weight of one or more active ingredients; and
c) the balance one or more diluents or carriers.
In one embodiment of this aspect, the activator compositions comprise:
a) from about 5% to about 8% by weight of one or more catalysts;
b) from about 0.5% to about 10% by weight of a peroxide stabilizing system containing;
  i) from about 10% to about 90% by weight of one or more metal chelants;
  ii) from about 10% to about 90% by weight of one or more peroxide stabilizers;
  iii) from about 10% to about 90% by weight of one or more composition integrity agents; and
c) the balance one or more diluents or carriers.

In another embodiment of this aspect, the activator compositions comprise:
a) from about 7% to about 20% by weight of one or more catalysts;
b) from about 0.5% to about 10% by weight of a peroxide stabilizing system containing;
  i) from about 10% to about 90% by weight of one or more metal chelants;
  ii) from about 10% to about 90% by weight of one or more peroxide stabilizers;
  iii) from about 10% to about 90% by weight of one or more composition integrity agents; and
c) the balance one or more diluents or carriers.

Viscosity Control Agents

The disclosed activator compositions can comprise from about 0.5% to about 5% by weight of one or more viscosity control agents. On category of suitable viscosity control agents are the copolymers of itaconate monoesters having the formula:

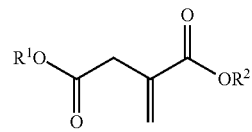

wherein one of $R^1$ and $R^2$ are hydrogen and the other of $R^1$ and $R^2$ is —$(CH_2CH_2O)_xR^3$, wherein x is an integer from about 1 to about 100. In one embodiment useful for the disclosed activator compositions, the index x is from about 10 to about 40, whereas in a further embodiment x is about 20. $R^3$ is $C_8$-$C_{30}$ alkyl, in one embodiment $R^3$ is $C_{12}$-$C_{20}$ alkyl. Non-limiting examples of viscosity control agents comprising an itaconate monomer includes acrylic acid or methacrylic acid/itaconic acid polyethoxyalkyl ester copolymers (INCI name: acrylates/Steareth-20 itaconate copolymer and acrylates/Ceteth-20 itaconate copolymer)), such as marketed by the firm National Starch, U.S.A. under the trademark Structure™ 2001 and Structure™ 3001, for example, acrylates/steareth-20 itaconate copolymer, acrylates/ceteth-20 itaconate methacrylates/steareth-20 itaconate copolymer, methacrylates/ceteth-20 itaconate acrylates/steareth-20 itaconate copolymer and acrylates/ceteth-20 itaconate copolymer.

Metal Chelants

Because the source of oxidizer, for example, hydrogen peroxide in the disclosed composition are susceptible to degradation in the presence of metals, the compositions can comprise one or more compatible metal chelants. Organic acids, for example, citric acid can be used as a metal chelant. The use of organic acids can have the added benefit as acting as a part of a buffer system to regulate the pH of the activator composition. Non-limiting examples of organic acids includes malonic acid, succinic acid, adipic acid fumaric acid, malic acid, maleic acid, citric acid, ethylenediamine tertraacetic acid, N-(hydroxyethyl)-ethylenediaminetriacetic acid, and the like.

Another category of chelants are those disclosed in U.S. Pat. Nos. 5,747,440, 4,138,478, 3,202,579, 3,542,918, 5,693, 854, 5,472,642, 4,983,315, and 5,284,972 each of which is incorporated herein in their entirety. Exemplary diamine dipolyacids suitable for use herein include ethylenediamine-N,N'-disuccinic acid (EDDS), ethylenediamine-N,N'-diglutaric acid (EDDG), 2-hydroxypropylenediamine-N,N'-disuccinic acid (HPDDS), all disclosed in European Patent EP0687292, ethylenedicysteic acid (EDC) disclosed in U.S.

Pat. No. 5,693,854, diaminoalkyldi(sulfosuccinic acids) (DDS) disclosed in U.S. Pat. No. 5,472,642 and EDDHA (ethylenediamine-N—N'-bis(orthohydroxyphenyl acetic acid)), a method of preparation of which is disclosed in EP331556. A preferred monoamine monoamide-N,N'-di-polyacid is glycinamide-N,N'-disuccinic acid (GADS), described in U.S. Pat. No. 4,983,315.

In one example sodium stannate is used as a chelant.

Peroxide Stabilizers

The disclosed activator compositions can comprise one or more peroxide stabilizers. One category includes diphosphonic acids, for example hydroxyethane-diphosphonic acid available as CUBLEN™ K 60 from AE Chemie. Other non-limiting examples includes the alkali metal salts of phosphoric acid, for example, trisodium phosphate, tripotassium phosphate, disodium phosphate, and the like.

Compositions

1. Colorant Systems

The disclosed compositions useful for coloring keratin-containing fibers are formulated in a manner that results in a homogeneous and stabilized colorant system. In general, the colorant system comprises, in order of addition:

A) from about 65% to about 75% by weight of a detangler/hair conditioner and emulsifier base;

B) from about 0.65% to about 2.5% by weight of a colorant precursor base;

C) from about 15% to about 25% by weight of an emollient base; and

D) from about 6.5% to about 11% by weight of an aesthetic base.

Base A

Base A comprises emulsifiers, compatible hair detangler agents, hair conditioning agents, and the like as disclosed herein. The following are non-limiting examples of Base A suitable for use in the disclosed colorant systems.

TABLE XIII

| Ingredients | A1 | A2 | A3 | A4 | A5 |
|---|---|---|---|---|---|
| Glycerin | 2.74 | 2.7 | 2.75 | 3 | 3 |
| EDTA | 0.75 | 0.75 | 0.76 | 0.82 | 0.8 |
| Sodium sulfite | 0.82 | 0.82 | 0.83 | 0.9 | 0.9 |
| PEG/PPG-120/10 trimethylolpropane trioleate laureth-2 | 1.37 | 1.3 | 1.37 | 1.5 | 1.4 |
| Poloxamer 185 | 1.37 | 1.3 | 1.37 | 1.5 | 1.49 |
| Aminomethyl propanol | 2.74 | 2.65 | 2.75 | 3 | 3 |
| Water | balance | balance | balance | balance | balance |

TABLE XIV

| Ingredients | A6 | A7 | A8 | A9 | A10 |
|---|---|---|---|---|---|
| Glycerin | 2.8 | 2.74 | 2.72 | 2.88 | 2.76 |
| EDTA | 0.75 | 0.75 | 0.75 | 0.79 | 0.8 |
| Sodium sulfite | 0.82 | 0.82 | 0.82 | 0.87 | 0.85 |
| PEG/PPG-120/10 trimethylolpropane trioleate laureth-2 | 1.37 | 1.4 | 1.6 | 1.44 | 1.52 |
| Poloxamer 185 | 1.37 | 1.4 | 1.36 | 1.44 | 1.52 |
| Aminomethyl propanol | 2.75 | 2.7 | 2.72 | 2.88 | 2.95 |
| Water | balance | balance | balance | balance | balance |

TABLE XV

| Ingredients | A11 | A12 | A13 | A14 | A15 |
|---|---|---|---|---|---|
| Glycerin | 2.73 | 2.71 | 2.75 | 3.1 | 3.1 |
| EDTA | 0.75 | 0.75 | 0.71 | 0.75 | 0.74 |
| Sodium sulfite | 0.82 | 0.82 | 0.81 | 0.88 | 0.9 |
| PEG/PPG-120/10 trimethylolpropane trioleate laureth-2 | 1.36 | 1.33 | 1.36 | 1.5 | 1.4 |
| Poloxamer 185 | 1.36 | 1.33 | 1.36 | 1.5 | 1.49 |
| Aminomethyl propanol | 2.73 | 2.72 | 2.75 | 3.1 | 3 |
| Water | balance | balance | balance | balance | balance |

Base B

Base B comprises one or more colorant precursors and one or more antioxidants.

The following are non-limiting examples of the relative amounts of a colorant composition to antioxidant suitable for preparing a Base B according to the present disclosure.

TABLE XVI

| Ingredient | B1 | B2 | B3 | B4 | B5 | B6 | B7 | B8 |
|---|---|---|---|---|---|---|---|---|
| Colorant composition | 68.6 | 61.5 | 54.9 | 39.8 | 18.4 | 74.0 | 66.6 | 60.4 |
| antioxidant | 31.4 | 38.5 | 45.1 | 60.2 | 81.6 | 26.0 | 33.4 | 39.6 |

Non-limiting examples of Base B suitable for use in the disclosed compositions include:

TABLE XVII

| Ingredients | B9 | B10 | B11 | B12 | B13 |
|---|---|---|---|---|---|
| 1,4-phenylenediamine | 2.9 | 2.4 | 2.5 | 2.7 | 6.9 |
| 4-aminophenol | 2.0 | 2.2 | 13.9 | 13.5 | 15.6 |
| 4-amino-2-hydroxytoluene | 19.8 | 19.4 | 25.1 | 25.0 | 26.0 |
| 2-nitro-N-(2-hydroxyethyl)aniline (HC Yellow 2) | 6.6 | 6.6 | — | — | 3.9 |
| 4-(3-hydroxypropylamino)-3-nitrophenol | 9.2 | 9.4 | 11.1 | 11.5 | 21.6 |
| 1-hydroxyethyl-4,5-diamino pyrazole sulfate | 19.8 | 18.2 | — | — | — |
| 4-amino-3-nitrophenol | — | — | 13.9 | 12.9 | — |
| Erythorbic acid | 39.7 | 41.8 | 33.5 | 34.4 | 26.0 |

TABLE XVIII

| Ingredients | B14 | B15 | B16 | B17 | B18 |
|---|---|---|---|---|---|
| 1,4-phenylenediamine | 27.4 | 28.0 | 14.5 | 14.5 | 21.8 |
| 4-aminophenol | 11.4 | 11.3 | 26.2 | 25.0 | 4.9 |
| 2-nitro-N-(2-hydroxyethyl)aniline (HC Yellow 2) | — | — | 1.0 | 1.1 | — |
| 3-aminophenol | 9.6 | 9.6 | — | — | 3.4 |
| 1,3-dhydroxybenzene | 9.1 | 9.3 | 23.1 | 26.4 | 21.8 |
| 4-chloro-1,3-dihydroxybenzene | 15.1 | 16.0 | — | — | — |
| 1-naphthol | — | — | 3.8 | 2.1 | — |
| 1-hydroxy-4-(4-methylanilino)-anthracene-9,10-dione (DC violet 2) | — | — | — | — | 1.9 |
| N,N-bis(2-hydroxyethyl)-1,4-phenylenediamine | — | — | — | — | 1.1 |
| Erythorbic acid | 27.5 | 25.8 | 31.4 | 30.9 | 45.1 |

TABLE XIX

| Ingredients | B19 | B20 | B21 | B22 | B23 |
|---|---|---|---|---|---|
| 1,4-phenylenediamine | 11.3 | 10.9 | 5.5 | 5.1 | 5.1 |
| 4-aminophenol | 12.0 | 12.1 | 2.0 | 3.0 | 29.5 |
| 2-nitro-N-(2-hydroxyethyl)aniline | — | — | — | — | 0.6 |

TABLE XIX-continued

| Ingredients | B19 | B20 | B21 | B22 | B23 |
|---|---|---|---|---|---|
| (HC Yellow 2) | | | | | |
| 1,3-dhydroxybenzene | 4.2 | 4.0 | — | — | 23.1 |
| 4-chloro-1,3-dihydroxybenzene | 6.0 | 6.6 | 3.0 | 2.8 | |
| 1-naphthol | — | — | — | — | 3.1 |
| 1-hydroxy-4-(4-methylanilino)-anthracene-9,10-dione (DC violet 2) | 1.0 | 1.0 | 1.1 | 1.2 | — |
| N,N-bis(2-hydroxyethyl)-1,4-phenylenediamine | 1.5 | 1.5 | 2.0 | 2.0 | — |
| 2-methyl-1,3-dihydroxybenzene | — | — | 2.7 | 2.1 | — |
| Erythorbic acid | 64.0 | 63.9 | 83.7 | 83.8 | 38.6 |

TABLE XX

| Ingredient | B24 | B25 | B26 | B27 | B28 | B29 | B30 | B31 |
|---|---|---|---|---|---|---|---|---|
| Colorant composition | 84.4 | 84.8 | 82.5 | 83.9 | 88.0 | 80.2 | 84.5 | 84.3 |
| antioxidant | 15.6 | 15.2 | 17.5 | 16.1 | 12.0 | 19.8 | 15.5 | 15.7 |

TABLE XXI

| Ingredients | B32 | B33 | B34 | B35 | B36 |
|---|---|---|---|---|---|
| 1,4-phenylenediamine | 38.9 | 40 | 38.9 | 38.8 | 37.2 |
| 1,3-dihydroxybenzene | 18.2 | 17.3 | 18.2 | 18.1 | 21.5 |
| 2,4-diaminophenoxyethanol sulfate | 6.5 | 6.5 | 6.3 | 6.4 | 5.9 |
| 3-aminophenol | 14.3 | 14.1 | 14.7 | 14.3 | 14.1 |
| N,N-bis(2-hydroxyethyl)-1,4-phenylenediamine | 6.5 | 6.5 | 6.3 | 6.4 | 5.9 |
| Erythorbic acid | 15.6 | 15.6 | 15.6 | 16 | 15.4 |

Base C

Base C comprises emollients and other ingredients that facilitate the even spreading of the colorant compositions onto keratin-containing fibers, as well as ingredients which allow the compositions to pass into the pores of the fibers. The following are non-limiting examples of Base C suitable for use in the disclosed colorant systems.

TABLE XXII

| Ingredients | C1 | C2 | C3 | C4 | C5 |
|---|---|---|---|---|---|
| Cetearyl alcohol | 27.4 | 27.5 | 28.2 | 26.2 | 26.3 |
| Cetearyl alcohol dicetyl phosphate Ceteth-10 phosphate | 27.3 | 27.5 | 25.7 | 26.2 | 26.3 |
| Cetyl alcohol | 27.3 | 25 | 25.7 | 26.2 | 26.3 |
| Ceteareth-20 | 4.5 | 5 | 5.1 | 5.4 | 5.3 |
| PPG-5 Ceteth-20 | 4.5 | 5 | 5.1 | 5.4 | 5.3 |
| Cetyl PEG/PPG-10/1 dimethicone | 4.5 | 5 | 5.1 | 5.3 | 5.3 |
| Laureth-2 | 4.5 | 5 | 5.1 | 5.3 | 5.2 |

TABLE XXIII

| Ingredients | C6 | C7 | C8 | C9 | C10 |
|---|---|---|---|---|---|
| Cetearyl alcohol | 25.7 | 25.8 | 25.7 | 25.5 | 25.6 |
| Cetearyl alcohol dicetyl phosphate Ceteth-10 phosphate | 25.7 | 25.7 | 25.8 | 25.5 | 25.6 |
| Cetyl alcohol | 25.7 | 25.7 | 25.7 | 25.5 | 25.6 |
| Ceteareth-20 | 5.7 | 5.7 | 5.7 | 5.9 | 5.8 |
| PPG-5 Ceteth-20 | 5.7 | 5.7 | 5.7 | 5.9 | 5.8 |
| Cetyl PEG/PPG-10/1 dimethicone | 5.7 | 5.7 | 5.7 | 5.8 | 5.8 |
| Laureth-2 | 5.8 | 5.7 | 5.7 | 5.9 | 5.8 |

Base D

Base D comprises UV protectants, aesthetics, for example, fragrances, pH adjusters, pearlizers, vitamins, keratin tissue restorers, and the like as disclosed herein. The following are non-limiting examples of Base D suitable for use in the disclosed colorant systems.

TABLE XXIV

| Ingredients | D1 | D2 | D3 | D4 | D5 |
|---|---|---|---|---|---|
| Oleic acid | 21.0 | 21.1 | 35.3 | 16.0 | 36.6 |
| Covabsorb ™ EW | 0.05 | 0.05 | 0.089 | 0.04 | 0.09 |
| Benzyl alcohol | 10.5 | 10.6 | 17.7 | 8.0 | 18.3 |
| fragrance | 10.5 | 10.6 | 17.7 | 8.0 | 18.3 |
| Laurolyl lysine | 0.001 | 0.001 | 0.002 | 0.0008 | 0.002 |
| Tocopheryl acetate | 0.001 | 0.001 | 0.002 | 0.0008 | 0.002 |
| Ammonium hydroxide | | | | | 18.3 |
| Lipidami ™ Caviar | 0.1 | 0.11 | 0.2 | 0.08 | 0.18 |
| Covapearl ™ star silver 937 | 2.6 | 2.6 | 7.9 | 3.6 | 8.2 |
| Covapearl ™ rich gold 230 AS | 2.6 | 2.1 | — | — | — |
| nascent water | balance | balance | balance | balance | balance |

TABLE XXV

| Ingredients | D6 | D7 | D8 | D9 | D10 |
|---|---|---|---|---|---|
| Oleic acid | 30.9 | 21.1 | 24.0 | 19.7 | 35.3 |
| Covabsorb EW | 0.08 | 0.05 | 0.08 | 0.06 | 0.05 |
| Benzyl alcohol | 15.5 | 10.6 | 10.2 | 10.2 | 17.7 |
| fragrance | 15.5 | 10.6 | 10.2 | 10.2 | 17.7 |
| Laurolyl lysine | 0.002 | 0.001 | 0.001 | 0.001 | 0.002 |
| Tocopheryl acetate | 0.002 | 0.001 | 0.001 | 0.001 | 0.002 |
| Lipidami ™ Caviar | 0.15 | 0.11 | 0.1 | 0.1 | 0.2 |
| Covapearl ™ star silver 937 | 7.0 | 4.5 | 2.6 | 3.6 | 6..5 |
| Covapearl ™ star bronze 8302 | — | 0.2 | 2.6 | 2.1 | — |
| Ammonium hydroxide | balance | balance | balance | balance | balance |

TABLE XXVI

| Ingredients | D11 | D12 | D13 | D14 | D15 |
|---|---|---|---|---|---|
| Oleic acid | 33.5 | 34 | 33.2 | 33.2 | 33.5 |
| Covabsorb EW | 0.08 | 0.08 | 0.08 | 0.08 | 0.08 |
| Benzyl alcohol | 16.8 | 16.8 | 16.5 | 16.5 | 16.8 |
| fragrance | 16.8 | 16.5 | 16.5 | 16.5 | 16.8 |
| Laurolyl lysine | 0.002 | 0.002 | 0.002 | 0.002 | 0.002 |
| Tocopheryl acetate | 0.002 | 0.002 | 0.002 | 0.002 | 0.002 |
| Lipidami ™ Caviar | 0.17 | 0.19 | 0.17 | 0.17 | 0.17 |
| Covapearl ™ bright 933 | 6.7 | 6.7 | 6.7 | 6.2 | 6.2 |
| Covapearl ™ light brown 803 | 0.8 | 0.8 | 0.8 | 1.5 | 1.5 |
| Ammonium hydroxide | balance | balance | balance | balance | balance |

Keratin-Containing Fiber Colorant Compositions

The following are non-limiting examples of compositions useful for coloring keratin-containing fibers.

Examples 1-3

The following is a non-limiting example of the procedure for preparing a colorant system which provides a red-color tint, base, or keratin-containing fiber color. The disclosed examples can be used on any type of keratin-containing fiber, especially human hair, either by a single user or applied by a professional, i.e., a stylist. The effect produced on keratin-containing fibers is reproducible and the color obtained thereby is homogeneous.

To a main formulation vessel is charged colorant Base A8 (71.64 equiv.) as exemplified in Table XI. The admixture is heated to from about 75° C. to about 80° C. Separately, colorant Base B is prepared by admixing colorant composition 2 as exemplified in Table I with an antioxidant to provide the following colorant composition base:

| Ingredients | Weight % |
|---|---|
| 1,4-phenyldnediamine | 2.9 |
| 4-aminophenol | 2.0 |
| 4-amino-2-hydroxytoluene | 19.8 |
| 1-nitro-N-(2-hydroxyethyl)aniline (HC Yellow 2) | 6.6 |
| 4-(3-hydroxypropylamino)-3-nitropenol | 9.3 |
| 1-hydroxyethyl-4,5-diaminopyrazole sulfate | 19.8 |
| erythorbic acid | 39.6 |

The colorant base (1.5 equiv.) is then added to the formulation and the resulting admixture is thoroughly stirred. Depending upon the choice of the formulator, the ingredients that comprise the colorant base can be added individually in any order desired.

In a separate vessel, Base C3, as exemplified in Table XVI, is prepared by admixing the listed ingredients. The order of addition of the ingredients that comprise Base C3 is any order that is convenient to the formulator and that provides a homogeneous composition. Base C3 is then pre-heated to about 80° C. and then 19.5 equivalents are added to the vessel containing Bases A and B with high speed efficient mixing. After stirring for approximately 30 minutes or until homogeneous, the vessel is cooled to a temperature of from about 45° C. to about 50° C. and Base D5 (5.47 equiv.), as exemplified in Table XVII, is added in the order in which the ingredients are listed.

In a like manner, Base A7, colorant No. 8, Base C4 and Base D6 are combined to produce the composition of Example 2. In a similar like manner, Base A6, colorant No. 15, Base C5 and Base D5 are combined to produce the composition of Example 3. The resulting compositions Examples 1-3 comprise the following ingredients in the following approximate amounts on a % weight/weight basis.

TABLE XXVII

| Ingredients | EX 1 | EX 2 | EX 3 |
|---|---|---|---|
| Glycerin | 2.0 | 2.0 | 2.0 |
| EDTA | 0.55 | 0.55 | 0.55 |
| sodium sulfite | 0.6 | 0.6 | 0.6 |
| PEG/PPG-120/10 trimethylolpropane trioleate laureth-2 | 1 | 1 | 1 |
| Poloxamer ™ 185 | 1 | 1 | 1 |
| aminomethyl propanol | 2 | 2 | 2 |
| erythorbic acid | 0.6 | 0.6 | 0.6 |
| 1,4-phenylenediamine | 0.044 | 0.045 | 0.16 |
| 4-aminophenol | 0.03 | 0.25 | 0.35 |
| 4-amino-2-hydroxytoluene | 0.3 | 0.45 | 0.6 |
| 2-nitro-N-(2-hydroxyethyl)aniline (HC Yellow 2) | 0.1 | — | 0.09 |
| 4-(3-hydroxypropylamino)-3-nitrophenol | 0.14 | 0.2 | 0.5 |
| 1-hydroxyethyl-4,5-diamino pyrazole sulfate | 0.3 | — | — |
| 4-amino-3-nitrophenol | — | 0.25 | — |
| Cetearyl alcohol | 5.5 | 4.9 | 5.5 |
| Cetearyl alcohol dicetyl phosphate ceterh-10 phosphate | 5 | 4.9 | 5 |
| Cetyl alcohol | 5 | 4.9 | 5 |
| Ceteareth-20 ™ | 1 | 1 | 1 |
| PPG-5 Ceteth-20 ™ | 1 | 1 | 1 |
| Cetyl PEG/PPG-10/1 dimethicone | 1 | 1 | 1 |
| Laureth-2 | 1 | 1 | 1 |
| Oleic acid | 2 | 2 | 2 |
| Covabsorb ™ EW | 0.005 | 0.005 | 0.005 |
| Benzyl alcohol | 1 | 1 | 1 |

TABLE XXVII-continued

| Ingredients | EX 1 | EX 2 | EX 3 |
|---|---|---|---|
| fragrance | 1 | 1 | 1 |
| Laurolyl lysine | 0.0001 | 0.0001 | 0.0001 |
| Tocopheryl acetate | 0.0001 | 0.0001 | 0.0001 |
| Ammonium hydroxide | 1 | 2 | 1 |
| Lipidami ™ caviar | 0.01 | 0.01 | 0.01 |
| Covapearl ™ star silver 9372 | 0.45 | 0.45 | 0.45 |
| water | balance | balance | balance |

The resulting Examples 1-3 were found to have the following properties:

TABLE XXVIII

| EX. | Alkalinity (%) | Viscosity (cps) | Vis/RTA (cps) | Spec. gr. g/mL | pH | pH/RTA |
|---|---|---|---|---|---|---|
| 1 | 1.17 | 334,300 | 375,000 | 1.004 | 8.56 | 8.3 |
| 2 | 0.78 | 210,900 | 159,300 | 0.996 | 10.04 | 9.27 |
| 3 | 0.75 | 289,000 | 281,000 | 0.989 | 10.12 | 9.37 |

The following are non-limiting examples of a colorant system which provides a brown-color tint, base, or keratin-containing fiber color. Examples 4-6 can be prepared in the manner described herein above for Example 1.

Example 4 comprises Base A2, colorant No. 18, Base C5 and Base D1. Example 5 comprises Base A1, colorant No. 22, Base C1 and Base D6. Example 6 comprises Base A3, colorant No. 30, Base C3 and Base D3. The resulting compositions Examples 4-6 comprise the following ingredients in the following approximate amounts on a % weight/weight basis.

TABLE XXIX

| Ingredients | EX 4 | EX 5 | EX 6 |
|---|---|---|---|
| Glycerin | 2.0 | 2.0 | 2.0 |
| EDTA | 0.55 | 0.55 | 0.55 |
| sodium sulfite | 0.6 | 0.6 | 0.6 |
| PEG/PPG-120/10 trimethylolpropane trioleate laureth-2 | 1 | 1 | 1 |
| Poloxamer ™ 185 | 1 | 1 | 1 |
| aminomethyl propanol | 2 | 2 | 2 |
| erythorbic acid | 0.6 | 0.6 | 0.6 |
| 1,4-phenylenediamine | 0.6 | 0.27 | 0.29 |
| 4-aminophenol | 0.25 | 0.5 | 0.065 |
| 3-aminophenol | 0.21 | — | 0.045 |
| 1,3-dihydroxybenzene | 0.2 | 0.44 | 0.29 |
| 4-chloro-1,3-dihydroxybenzene | 0.33 | — | — |
| 2-nitro-N-(2-hydroxyethyl)aniline | — | 0.02 | — |
| 1-naphthol | — | 0.072 | — |
| 1-hydroxy-4-(4-methylanilino)-anthracene-9,10-dione (DC violet 2) | — | 0.02 | — |
| N,N-bis(2-hydroxyethyl)-1,4-phenylenediamine sulfate | — | — | 0.015 |
| Cetearyl alcohol | 5 | 6.0 | 5.5 |
| Cetearyl alcohol dicetyl phosphate ceterh-10 phosphate | 5 | 6.0 | 5 |
| Cetyl alcohol | 5 | 6.0 | 5 |
| Ceteareth-20 ™ | 1 | 1 | 1 |
| PPG-5 Ceteth-20 | 1 | 1 | 1 |
| Cetyl PEG/PPG-10/1 dimethicone | 1 | 1 | 1 |
| Laureth-2 | 1 | 1 | 1 |
| Oleic acid | 2 | 2 | 2 |
| Covabsorb ™ EW | 0.005 | 0.005 | 0.005 |
| Benzyl alcohol | 1 | 1 | 1 |
| fragrance | 1 | 1 | 1 |
| Laurolyl lysine | 0.0001 | 0.0001 | 0.0001 |
| Tocopheryl acetate | 0.0001 | 0.0001 | 0.0001 |
| Ammonium hydroxide | 5 | 5 | 1.2 |
| Lipidami ™ caviar | 0.01 | 0.01 | 0.01 |
| Covapearl ™ star silver 9372 | 0.43 | 0.25 | 0.45 |
| Covapearl ™ star bronze 8302 | 0.02 | — | — |

TABLE XXIX-continued

| Ingredients | EX 4 | EX 5 | EX 6 |
|---|---|---|---|
| Covapearl ™ rich gold 230 AS | — | 0.2 | — |
| water | balance | balance | balance |

The resulting Examples 4-6 were found to have the following properties:

TABLE XXX

| EX. | Alkalinity (%) | Viscosity (cps) | Vis/RTA (cps) | Spec. gr. g/mL | pH | pH/RTA |
|---|---|---|---|---|---|---|
| 4 | 1.97 | 301,500 | 325,00 | 0.968 | 10.95 | 10.11 |
| 5 | 1.92 | 246,800 | 378,100 | 0.988 | 11 | 9.64 |
| 6 | 1.37 | 165,600 | 25,300 | 0.947 | 10.35 | 9.46 |

The following are non-limiting examples of a colorant system which provides a blonde color tint, base, or keratin-containing fiber color. Examples 7-9 can be prepared in the manner described herein above for Example 1.

Example 7 comprises Base A4, colorant No. 34, Base C3 and Base D4. Example 8 comprises Base A5, colorant No. 36, Base C3 and Base D4. Example 9 comprises Base A4, colorant No. 43, Base C2 and Base D2. The resulting compositions Examples 7-9 comprise the following ingredients in the following approximate amounts on a % weight/weight basis.

TABLE XXXI

| Ingredients | EX 7 | EX 8 | EX 9 |
|---|---|---|---|
| glycerin | 2.0 | 2.0 | 2.0 |
| EDTA | 0.55 | 0.55 | 0.55 |
| sodium sulfite | 0.6 | 0.6 | 0.6 |
| PEG/PPG-120/10 trimethylolpropane trioleate laureth-2 | 1 | 1 | 1 |
| Poloxamer ™ 185 | 1 | 1 | 1 |
| aminomethyl propanol | 2 | 2 | 2 |
| erythorbic acid | 0.6 | 0.6 | 0.6 |
| 1,4-phenylenediamine | 0.15 | 0.055 | 0.08 |
| 4-aminophenol | 0.12 | 0.015 | 0.46 |
| 1,3-dihydroxybenzene | 0.042 | — | 0.36 |
| 4-chloro-1,3-dihydroxybenzene | 0.06 | 0.022 | — |
| 1-hydroxy-4-(4-methylanilino)-anthracene-9,10-dione (DC violet 2) | 0.01 | 0.008 | — |
| N,N-bis(2-hydroxyethyl)-1,4-phenylenediamine sulfate | 0.015 | — | — |
| 2-methyl-1,3-dihydroxybenzene | — | 0.02 | — |
| 2-nitro-N-(2-hydroxyethyl)aniline (HC Yellow 2) | — | — | 0.01 |
| 1-naphthol | — | — | 0.048 |
| Cetearyl alcohol | 5.5 | 5.5 | 5.5 |
| Cetearyl alcohol dicetyl phosphate ceterh-10 phosphate | 5 | 5 | 5 |
| Cetyl alcohol | 5 | 5 | 5.5 |
| Ceteareth-20 ™ | 1 | 1 | 1 |
| PPG-5 Ceteth-20 ™ | 1 | 1 | 1 |
| Cetyl PEG/PPG-10/1 dimethicone | 1 | 1 | 1 |
| Laureth-2 | 1 | 1 | 1 |
| Oleic acid | 2 | 2 | 2 |
| Covabsorb ™ EW | 0.005 | 0.005 | 0.005 |
| Benzyl alcohol | 1 | 1 | 1 |
| fragrance | 1 | 1 | 1 |
| Laurolyl lysine | 0.0001 | 0.0001 | 0.0001 |
| Tocopheryl acetate | 0.0001 | 0.0001 | 0.0001 |
| Ammonium hydroxide | 8 | 8 | 5 |
| Lipidami caviar ™ | 0.01 | 0.01 | 0.01 |
| Covapearl ™ star silver 9372 | 0.45 | 0.45 | 0.25 |
| Covapearl ™ rich gold 230 AS | — | — | 0.2 |
| water | balance | balance | balance |

The resulting Examples 7-9 were found to have the following properties:

TABLE XXXII

| EX. | Alkalinity (%) | Viscosity (cps) | Vis/RTA (cps) | Spec. gr. g/mL | pH | pH/RTA |
|---|---|---|---|---|---|---|
| 7 | 1.8 | 273,400 | 265,600 | 0.954 | 11.13 | 9.51 |
| 8 | 2.28 | 353,100 | 354,600 | 0.934 | 5-11 | 10.51 |
| 9 | 1.91 | 173,400 | 343,700 | 0.965 | 10.31 | 9.97 |

The following are non-limiting examples of a colorant system which provides a black-color tint, base, or keratin-containing fiber color. Examples 10-12 can be prepared in the manner described herein above for Example 1.

Example 10 comprises Base A4, colorant No. 46, Base C6 and Base D11. Example 11 comprises Base A4, colorant No. 60, Base C6 and Base D11. Example 12 comprises Base A4, colorant No. 52, Base C6 and Base D11. The resulting compositions Examples 10-12 comprise the following ingredients in the following approximate amounts on a % weight/weight basis.

TABLE XXXIII

| Ingredients | EX 10 | EX 11 | EX 12 |
|---|---|---|---|
| glycerin | 2.0 | 2.0 | 2.0 |
| EDTA | 0.55 | 0.55 | 0.55 |
| sodium sulfite | 0.6 | 0.6 | 0.6 |
| PEG/PPG-120/10 trimethylolpropane trioleate laureth-2 | 1 | 1 | 1 |
| Poloxamer ™ 185 | 1 | 1 | 1 |
| aminomethyl propanol | 2 | 2 | 2 |
| erythorbic acid | 0.6 | 0.6 | 0.6 |
| 1,4-phenylenediamine | 1.5 | 1.65 | 1.44 |
| 1,3-dihydroxybenzene | 0.7 | 0.65 | 0.75 |
| 2,4-diaminophenoxyethanol sulfate | 0.25 | 0.25 | 0.26 |
| 3-aminophenol | 0.55 | 0.47 | 0.54 |
| N,N-bis(2-hydroxyethyl)-1,4-phenylenediamine sulfate | 0.25 | 0.25 | 0.26 |
| Cetearyl alcohol | 4.5 | 4.5 | 4.5 |
| Cetearyl alcohol dicetyl phosphate ceteth-10 phosphate | 4.5 | 4.5 | 4.5 |
| Cetyl alcohol | 4.5 | 4.5 | 4.5 |
| Ceteareth-20 ™ | 1 | 1 | 1 |
| PPG-5 Ceteth-20 ™ | 1 | 1 | 1 |
| Cetyl PEG/PPG-10/1 dimethicone | 1 | 1 | 1 |
| Laureth-2 | 1 | 1 | 1 |
| Oleic acid | 2 | 2 | 2 |
| Covabsorb ™ EW | 0.005 | 0.005 | 0.005 |
| Benzyl alcohol | 1 | 1 | 1 |
| fragrance | 1 | 1 | 1 |
| Laurolyl lysine | 0.0001 | 0.0001 | 0.0001 |
| Tocopheryl acetate | 0.0001 | 0.0001 | 0.0001 |
| Ammonium hydroxide | 1.5 | 1.5 | 1.5 |
| Lipidami caviar ™ | 0.01 | 0.01 | 0.01 |
| Covapearl ™ bright 933 | 0.4 | 0.4 | 0.4 |
| Covapearl ™ light brown 803 | 0.05 | 0.05 | 0.05 |
| water | balance | balance | balance |

Example 10 was found to have the following properties:

TABLE XXXIV

| EX. | Alkalinity (%) | Viscosity (cps) | Vis/RTA (cps) | Spec. gr. g/mL | pH | pH/RTA |
|---|---|---|---|---|---|---|
| 10 | 1.97 | 301,500 | 265,700 | 0.968 | 10.95 | 10.11 |

2. Activator Compositions

The following are non-limiting examples of activator compositions useful for coloring keratin-containing fibers. The disclosed colorant systems can be combined during use with the herein disclosed activator compositions. The following are non-limiting iterations of activator compositions according to this embodiment.

TABLE XXXV

| Ingredients | AC1 | AC2 | AC3 | AC4 | AC5 |
|---|---|---|---|---|---|
| Emulsifiers/surfactants | 3.6 | 3.1 | 2.9 | 3.9 | 4 |
| Viscosity control agents | 1.2 | 1.2 | 1.05 | 1.1 | 1.4 |
| Chelants | 0.35 | 0.5 | 0.35 | 0.44 | 0.3 |
| Peroxide stabilizers | 0.27 | 0.3 | 0.25 | 0.31 | 0.28 |
| Hydrogen peroxide | 6 | 6.2 | 5.88 | 6 | 6.05 |
| Carriers | balance | balance | balance | balance | balance |

The disclosed activator compositions useful for coloring keratin-containing fibers are formulated in a manner that results in a homogeneous and stabilized activator composition. In general, the activator composition comprises, in order of addition:
  A) from about 60% to about 85% by weight of a viscosity control/stabilizer base;
  B) from about 5% to about 10% by weight of a emulsifier base; and
  C) from about 10% to about 50% by weight of an oxidizer/catalyst base.

Stabilizer Base

The stabilizer base comprises metal chelants, buffers, viscosity control agents, and the like. The following are non-limiting examples of stabilizer bases.

TABLE XXXVI

| Ingredients | SB1 | SB2 |
|---|---|---|
| Glycerin | 0.25 | 0.33 |
| Disodium phosphate | 0.06 | 0.08 |
| sodium stannate | 0.06 | 0.08 |
| Pentasodium pentetate | 0.38 | 0.49 |
| Acrylates/steareth-20 itaconate copolymer | 1.5 | 2.0 |
| water | balance | balance |

Emulsifier Base

The emulsifier base comprises emulsifier, surfactants, antioxidants, and the like. The following are non-limiting examples of stabilizer bases

TABLE XXXVII

| Ingredients | EB1 | EB2 |
|---|---|---|
| Polyacrylaminde/$C_{13}$-$C_{14}$ isoparaffin/laureth-7 | 6.0 | 6.0 |
| Stearyl alcohol | 28.3 | 28.7 |
| Ceteareth-25 | 15.1 | 15.0 |
| Etidronic acid | 1.2 | 1.2 |
| Water* | balance | balance |

*Includes water delivered as part of the ingredients

Oxidizer/Catalyst Base

The emulsifier base comprises one or more oxidizers or colorant precursor reaction catalysts and antioxidants/stabilizers. The following are non-limiting examples of the disclosed oxidizer/catalyst bases.

TABLE XXXVIII

| Ingredients | OB1 | OB2 |
|---|---|---|
| Etidronic acid | 0.69 | 0.34 |
| Hydrogen peroxide* | 34.6 | 34.7 |
| Water | balance | balance |

*Formulated as a 35% w/w solution - value reflects actual peroxide

Keratin-Containing Fiber Colorant Activator Compositions

The following are non-limiting examples of activator compositions useful for coloring keratin-containing fibers.

Examples 13-16

The following is a non-limiting example of the procedure for preparing an activator composition which can be used with any of the disclosed colorant systems to provide a color tint, base, or keratin-containing fiber color. The disclosed examples can be used on any type of keratin-containing fiber, especially human hair, either by a single user or applied by a professional, i.e., a stylist. The effect produced on keratin-containing fibers is reproducible and the color obtained by using the disclosed activators in combination with the disclosed colorant system provides a color that is homogeneous.

To a main formulation vessel is charged Stabilizer Base SB1 (78.46 equiv.) as exemplified in Table XXXVI. The admixture is heated to from about 70° C. to about 75° C. With high speed efficient stirring the contents of Emulsifier Base EB1 (8.3 equiv.) are added in the order listed in Table XXXVII. After the addition is complete and mixing has continued for at least about 10 minutes, the admixture is cooled to about 40° C. while the speed of the mixing devices is reduced to a medium-slow setting. The contents of Oxidizer Base OB1 (15.32 equiv.) is then added in the order listed in Table XXXVIII. After addition is complete, the solution is cooled to about 30° C. to about 35° C. After stirring for about 10 minutes the amount of hydrogen peroxide present and composition pH is checked and adjusted by the addition of additional hydrogen peroxide or pH adjuster, i.e., phosphate buffer. The following are non-limiting examples of the disclosed Activator compositions.

TABLE XXXIX

| Ingredients | EX 13 | EX 14 | EX 15 | EX 16 |
|---|---|---|---|---|
| Glycerin | 0.2 | 0.2 | 0.2 | 0.2 |
| Disodium phosphate | 0.05 | 0.05 | 0.07 | 0.07 |
| sodium stannate | 0.05 | 0.05 | 0.05 | 0.05 |
| Pentasodium pentetate | 0.3 | 0.3 | 0.3 | 0.3 |
| Acrylates/steareth-20 itaconate copolymer | 1.2 | 1.2 | 1.2 | 1.2 |
| Polyacrylaminde/$C_{13}$-$C_{14}$ isoparaffin/laureth-7 | 0.5 | 0.5 | 0.5 | 0.5 |
| Stearyl alcohol | 2.35 | 2.4 | 2.2 | 2.2 |
| Ceteareth-25 | 1.25 | 1.25 | 1.25 | 1.25 |
| Etidronic acid | 0.3 | 0.3 | 0.3 | 0.3 |
| Hydrogen peroxide | 17.14 | 34.28 | 17.14 | 34.28 |
| Water | balance | balance | balance | balance |

The resulting Examples 13-16 were found to have the following properties:

TABLE XXXX

| EX. | $H_2O_2$ (%) | Viscosity (cps)* | Spec. gr. g/mL | pH |
|---|---|---|---|---|
| 13 | 6.05 | 300-600 | 1.1 | 3.69 |
| 14 | 12.05 | 300-600 | 1.015 | 3.60 |

*Measured at LV3, 1.5 rpm, 1 min.

For activator compositions according to Example 13, the pH is measured at 38° C., however the pH can range from about 3.2 to about 3.8. The percent hydrogen peroxide can range from about 5.95 to about 6.05. The specific gravity can range from about 1.01 g/mL to about 1.1 g/mL.

For activator compositions according to Example 14, the pH is measured at 38° C., however the pH can range from about 3.2 to about 3.8. The percent hydrogen peroxide can range from about 11.95 to about 12.05. The specific gravity can range from about 1.01 g/mL to about 1.1 g/mL.

The pH-value of the disclosed compositions, i.e. after mixing with peroxide, can be from about 5 to about 12. In one embodiment the pH is from about 6 to about 11. In a further embodiment the pH is from about 6.8 to about 10.

Kits

Disclosed herein are kits for coloring keratin-containing fibers, comprising:
A) a colorant system, comprising:
a) one or more colorant precursors;
b) optionally one or more active ingredients; and
c) optionally one or more diluents or carriers; and
B) an activator composition, comprising;
a) one or more catalysts;
b) optionally one or more active ingredients; and
c) optionally one or more diluents or carriers.

In one embodiment the colorant system and the activator composition are contained in separate packages. Non-limiting examples of packages includes bottles, pouches, and the like. Bottles can comprise any material compatible with the colorant system and the activator composition, for example, glass, plastic, and the like. Bottles can be fitted with a metering device, i.e., a pump and can include volume markings. Pouches can also comprise suitable materials that are compatible with the colorant system and the activator composition.

In another embodiment, the kit can comprise a separate container for admixing the colorant system and the activator composition prior to use. In a still further embodiment, the kit can comprise a single package wherein the colorant system and activator system are contained in the same package, the colorant system and activator system kept separately from one another by a barrier that can be broken by a user such that the colorant system and activator system come into contact with one another to form a final keratin-containing fiber dyeing composition.

Optionally, the kit can contain instructions for use, wherein the instructions provide the user with one or more directions or options for use of the keratin-containing fiber dyeing composition. Non-limiting examples of instructions include time for allowing the keratin-containing fiber dyeing composition to form after combining the colorant system and the activator composition, directions relating to volume markings on one or more packages, and methods for disposal of one or more solutions generated in forming the keratin-containing fiber dyeing composition.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A composition for dyeing keratin-containing fibers, comprising:
A) a colorant system, comprising:
a) the following colorant precursors:
i) from about 10% to about 70% by weight of 1,4-phenylenediamine;
ii) from about 1% to about 35% by weight of 1,3-dihydroxybenzene;
iii) from about 1% to about 35% by weight of 2,4-diaminophenoxy-ethanol sulfate;
iv) from about 0.5% to about 35% by weight of 3-aminophenol; and
v) from about 0.5% to about 20% by weight of N,N-bis(2-hydroxyethyl) -1,4-phenylenediamine;
b) optionally one or more active ingredients; and
c) optionally one or more diluents or carriers; and
B) an activator composition, comprising;
a) one or more catalysts;
b) optionally one or more active ingredients; and
c) optionally one or more diluents or carriers.

2. The composition according to claim 1, wherein the colorant system comprises from about 0.15% to about 7% by weight of the composition.

3. The composition according to claim 1, wherein the colorant system comprises from about 0.5% to about 5% by weight of the composition.

4. The composition according to claim 1, wherein the colorant system comprises from about 2% to about 5% by weight of the composition.

5. The composition according to claim 4, comprising:
i) from about 1.44% to about 1.65% by weight of the composition 1,4-phenylenediamine;
ii) from about 0.65% to about 0.75% by weight of the composition 1,3-dihydroxybenzene;
iii) from about 0.25% to about 0.26% by weight of the composition 2,4-diaminophenoxy-ethanol sulfate;
iv) from about 0.47% to about 0.54% by weight of the composition 3-aminophenol; and
v) from about 0.25% to about 0.26% by weight of the composition N,N-bis(2-hydroxyethyl)-1,4-phenylenediamine.

6. The composition according to claim 1, comprising:
i) 1.5% by weight of the composition 1,4-phenylenediamine;
ii) 0.7% by weight of the composition 1,3-dihydroxybenzene;
iii) 0.25% by weight of the composition 2,4-diaminophenoxy-ethanol sulfate;
iv) 0.55% by weight of the composition 3-aminophenol; and
v) 0.25% by weight of the composition N,N-bis(2-hydroxyethyl)-1,4-phenylenediamine.

7. The composition according to claim 1, wherein the colorant system comprises one of more of the following:
a) from about 0.2% to about 1% by weight, of one or more hair detangling agents chosen from $C_{10}$-$C_{22}$ alkyl esters of alkoxylated trimethylolpropane, $C_{10}$-$C_{22}$ alkenyl mono-ene esters of alkoxylated trimethylolpropane, $C_{10}$-$C_{22}$ alkynyl mono-yne esters of alkoxylated trimethylol-propane, and mixtures thereof;
b) from about 0.005% to 0.05% by weight, of one or more UV absorbers chosen from ethylhexyl methoxycinnamate (octyl methoxy-cinnamate), methoxydibenzoylmethane, polyoxypropylene, polyoxyethylene ethers of aliphatic alcohols, ethylhexyl salicylate, and polyoxyethylene derivatives of hydroxy fatty acid containing fats and oils, and mixtures thereof; and
c) from about 0.1% to about 1.5% by weight, of one or more conditioning agents chosen from polyalkylene glycols, polypropylene glycols, polyalkylene glycol/polypropylene glycol copolymers.

8. The composition according to claim 1, wherein the activator composition comprises:
a) from about 5% to about 15% by weight of one or more catalysts;
b) from about 3% to about 10% by weight of one or more active ingredients; and
c) the balance one or more diluents or carriers.

9. The composition according to claim 1, wherein the activator composition comprises:
   a) from about 7% to about 20% by weight of one or more catalysts;
   b) from about 0.5% to about 10% by weight of a peroxide stabilizing system containing;
      i) from about 10% to about 90% by weight of one or more metal chelants;
      ii) from about 10% to about 90% by weight of one or more peroxide stabilizers;
      iii) from about 10% to about 90% by weight of one or more composition integrity agents; and
   c) the balance one or more diluents or carriers.

10. The composition according to claim 1, wherein the activator composition comprises from about 0.5% to about 10% by weight of a peroxide stabilizing system containing:
   i) from about 10% to about 90% by weight of one or more metal chelants;
   ii) from about 10% to about 90% by weight of one or more peroxide stabilizers;
   iii) from about 10% to about 90% by weight of one or more composition integrity agents.

11. A kit for dyeing keratin-containing fibers, wherein the kit comprises the following composition:
   A) a colorant system, comprising:
      a) the following colorant precursors:
         i) from about 10% to about 70% by weight of 1,4-phenylenediamine;
         ii) from about 1% to about 35% by weight of 1,3-dihydroxybenzene;
         iii) from about 1% to about 35% by weight of 2,4-diaminophenoxy-ethanol sulfate;
         iv) from about 0.5% to about 35% by weight of 3-aminophenol; and
         v) from about 0.5% to about 20% by weight of N,N-bis(2-hydroxyethyl)-1,4-phenylenediamine;
      b) optionally one or more active ingredients; and
      c) optionally one or more diluents or carriers; and
   B) an activator composition, comprising;
      a) one or more catalysts;
      b) optionally one or more active ingredients; and
      c) optionally one or more diluents or carriers.

12. The kit according to claim 11, wherein the colorant system comprises from about 2% to about 5% by weight of the composition.

13. The kit according to claim 12, comprising:
   i) from about 1.44% to about 1.65% by weight of the composition 1,4-phenylenediamine;
   ii) from about 0.65% to about 0.75% by weight of the composition 1,3-dihydroxybenzene;
   iii) from about 0.25% to about 0.26% by weight of the composition 2,4-diaminophenoxy-ethanol sulfate;
   iv) from about 0.47% to about 0.54% by weight of the composition 3-aminophenol; and
   v) from about 0.25% to about 0.26% by weight of the composition N,N-bis(2-hydroxyethyl)-1,4-phenylenediamine;

14. The kit according to claim 11, comprising:
   i) 1.5% by weight of the composition 1,4-phenylenediamine;
   ii) 0.7% by weight of the composition 1,3-dihydroxybenzene;
   iii) 0.25% by weight of the composition 2,4-diaminophenoxy-ethanol sulfate;
   iv) 0.55% by weight of the composition 3-aminophenol; and
   v) 0.25% by weight of the composition N,N-bis(2-hydroxyethyl)-1,4-phenylenediamine.

15. The kit according to claim 11, wherein the colorant system comprises one of more of the following:
   a) from about 0.2% to about 1% by weight, of one or more hair detangling agents chosen from $C_{10}$-$C_{22}$ alkyl esters of alkoxylated trimethylolpropane, $C_{10}$-$C_{22}$ alkenyl mono-ene esters of alkoxylated trimethylolpropane, $C_{10}$-$C_{22}$ alkynyl mono-yne esters of alkoxylated trimethylol-propane, and mixtures thereof;
   b) from about 0.005% to 0.05% by weight, of one or more UV absorbers chosen from ethylhexyl methoxycinnamate (octyl methoxy-cinnamate), methoxydibenzoyl-methane, polyoxypropylene, polyoxyethylene ethers of aliphatic alcohols, ethylhexyl salicylate, and polyoxyethylene derivatives of hydroxy fatty acid containing fats and oils, and mixtures thereof; and
   c) from about 0.1% to about 1.5% by weight, of one or more conditioning agents chosen from polyalkylene glycols, polypropylene glycols, polyalkylene glycol/polypropylene glycol copolymers.

16. The kit according to claim 11, wherein the activator kit comprises:
   a) from about 5% to about 15% by weight of one or more catalysts;
   b) from about 3% to about 10% by weight of one or more active ingredients; and
   c) the balance one or more diluents or carriers.

17. The kit according to claim 11, wherein the activator kit comprises:
   a) from about 7% to about 20% by weight of one or more catalysts;
   b) from about 0.5% to about 10% by weight of a peroxide stabilizing system containing;
      i) from about 10% to about 90% by weight of one or more metal chelants;
      ii) from about 10% to about 90% by weight of one or more peroxide stabilizers;
      iii) from about 10% to about 90% by weight of one or more kit integrity agents; and
   c) the balance one or more diluents or carriers.

18. The kit according to claim 11, wherein the activator kit comprises from about 0.5% to about 10% by weight of a peroxide stabilizing system containing:
   i) from about 10% to about 90% by weight of one or more metal chelants;
   ii) from about 10% to about 90% by weight of one or more peroxide stabilizers;
   iii) from about 10% to about 90% by weight of one or more kit integrity agents.

19. A kit according to claim 11, further comprising a package which contains the colorant system, a package which contains the activator composition and a container for admixing the colorant system and activator composition prior to use.

20. A kit according to claim 11, wherein the colorant system and activator system are contained in the same package, the colorant system and activator system kept separately from one another by a barrier that can be broken by a user such that the colorant system and activator system come into contact with one another to form a final keratin-containing fiber dyeing composition.

* * * * *